US012697348B2

(12) United States Patent
Wagner

(10) Patent No.: US 12,697,348 B2
(45) Date of Patent: Aug. 4, 2026

(54) COMPOSITIONS FOR PROMOTING LONGEVITY AND METHODS OF USING THE SAME

(71) Applicant: Vital Nutrition and Health Inc, Dallas, TX (US)

(72) Inventor: Paul Wagner, San Juan, PR (US)

(73) Assignee: VITAL NUTRITION AND HEALTH INC, Dallas, TX (US)

( * ) Notice: Subject to any disclaimer, the term of this patent is extended or adjusted under 35 U.S.C. 154(b) by 0 days.

(21) Appl. No.: 18/592,355

(22) Filed: Feb. 29, 2024

(65) Prior Publication Data

US 2025/0275998 A1 Sep. 4, 2025

(51) Int. Cl.

| | |
|---|---|
| *A61K 35/20* | (2006.01) |
| *A61K 31/05* | (2006.01) |
| *A61K 31/122* | (2006.01) |
| *A61K 31/132* | (2006.01) |
| *A61K 31/196* | (2006.01) |
| *A61K 31/197* | (2006.01) |
| *A61K 31/198* | (2006.01) |
| *A61K 31/375* | (2006.01) |
| *A61K 31/4188* | (2006.01) |
| *A61K 31/519* | (2006.01) |
| *A61K 31/7056* | (2006.01) |
| *A61K 31/7084* | (2006.01) |
| *A61K 31/714* | (2006.01) |
| *A61K 31/728* | (2006.01) |
| *A61K 38/39* | (2006.01) |

(52) U.S. Cl.
CPC .......... *A61K 31/7084* (2013.01); *A61K 31/05* (2013.01); *A61K 31/122* (2013.01); *A61K 31/132* (2013.01); *A61K 31/196* (2013.01); *A61K 31/197* (2013.01); *A61K 31/198* (2013.01); *A61K 31/375* (2013.01); *A61K 31/4188* (2013.01); *A61K 31/519* (2013.01); *A61K 31/7056* (2013.01); *A61K 31/714* (2013.01); *A61K 31/728* (2013.01); *A61K 35/20* (2013.01); *A61K 38/39* (2013.01)

(58) Field of Classification Search
CPC ....... A61Q 19/00; A61Q 19/08; A23L 33/155; A23L 5/44; A23L 33/15; A23L 33/10
See application file for complete search history.

(56) References Cited

U.S. PATENT DOCUMENTS

| | | |
|---|---|---|
| 6,479,069 B1 | 11/2002 | Hamilton |
| 2009/0110674 A1 | 4/2009 | Loizou |
| 2010/0254962 A1 | 10/2010 | Zehethofer |

FOREIGN PATENT DOCUMENTS

| | | |
|---|---|---|
| WO | WO-2021094947 A1 | 5/2021 |
| WO | WO-2021205237 A1 | 10/2021 |

OTHER PUBLICATIONS

Dietary supplement Wikipedia 2024 refered to Wikipedia 1994,) multivitamin supplement. pp 1-29.*
Thomas et al. CI inv. Aging, 2006, pp. 81-91.*
Candow et al. J. cli med, 2019, , pp. 1-15.*
Zmitek et a. Nutrients 2020, 12(618), pp. 1-13.*
John hopkins MEdicine, Nutritient suplmn, 2021, pp. 1-4.*
Czajka et al. Nutrition Research, 2018, 57, pp. 97-108. (Year: 2018).*
Amorim et al. J. spinal cord Medicine, 2018, 41, pp. 471-478. (Year: 2018).*
LifeCell Health. Muscle Anti-Aging Muscle Building Protein. https://www.lifecellhealth.com/product/anti-aging-muscle-building-protein/ (2024).
FDA Announces Qualified Health Claim for Cocoa Flavanols in High Flavanol Cocoa Powder and Reduced Risk of Cardiovascular Disease (Feb. 3, 2023).
Gokbel et al., The Effects of Coenzyme Q10 Supplementation on Performance During Repeated Bouts of Supramaximal Exercise in Sedentary Men. Journal of Strength and Conditioning Research 24 (1):97-102 (2010).
Raventos et al., Review: Health Effects of Cocoa Flavonoids. Food Science and Technology International 11 (3):159-176 (2005).
PCT/US2025/017986 International Search Report and Written Opinion dated Jun. 17, 2025.
PCT/US2025/017986 Invitation to Pay Additional Fees dated Apr. 21, 2025.

* cited by examiner

*Primary Examiner* — Tekchand Saidha
*Assistant Examiner* — Mohammad Y Meah
(74) *Attorney, Agent, or Firm* — WILSON SONSINI GOODRICH & ROSATI

(57) ABSTRACT

Disclosed herein are nutritional compositions aimed at promoting longevity and wellness. The compositions are formulated for oral intake and include a variety of nutrients and functional compounds such as proteins, creatine, antioxidants, vitamins, minerals, hyaluronic acid, biotin, CoQ10, spermidine, and one or more NAD⁺ precursors. These components may serve to enhance muscle health, antioxidant function, skin, hair and joint health, cellular and cardiovascular health, thus contributing to the overall vitality and lifespan of an individual.

16 Claims, No Drawings

COMPOSITIONS FOR PROMOTING LONGEVITY AND METHODS OF USING THE SAME

BACKGROUND OF THE INVENTION

Aging is a natural process accompanied by a gradual decline in bodily functions and systems. This is often marked by a weakened muscular system, reduced antioxidant function, progressive degradation of skin, hair and joint health, and less efficient cellular and cardiovascular functions. A lack of key nutrients and functional compounds often contributes to age-related issues.

SUMMARY OF THE INVENTION

Embodiments of the present disclosure, in some aspects, provide nutritional compositions intended to promote longevity and overall wellness. Example compositions provided herein comprise various nutrients and functional compounds that may confer positive health outcomes. For instance, certain embodiments provide a composition comprising antioxidants, proteins and amino acid derivatives, polyamines, vitamins, and precursors of nicotinamide adenine dinucleotide (NAD$^+$). The composition may be suitable for oral delivery concurrently with or as an alternative to a multi-supplement regimen comprising similar or identical nutrients and/or functional compounds. In some instances, compositions disclosed herein promote positive health outcomes including, but not limited to, cellular growth and metabolic support, skin and tissue health, cardiovascular health, antioxidant function, and longevity.

The above features and methods are of representative embodiments only and are not intended to limit the scope and breadth of the claims.

In one aspect, provided herein is a composition comprising eight or more of collagen, creatine or a derivative thereof, trans-resveratrol, vitamin C or a derivative thereof, coenzyme Q10 (CoQ10), spermidine, folate, or a derivative thereof, vitamin B12 or a derivative thereof, vitamin B5 or a derivative thereof, para-aminobenzoic acid (PABA), one or more precursors of NAD$^+$, hyaluronic acid, and biotin.

In one aspect, provided herein is a composition comprising eight or more of collagen, creatine or a derivative thereof, trans-resveratrol, vitamin C or a derivative thereof, coenzyme Q10 (CoQ10), spermidine, folate, or a derivative thereof, vitamin B12 or a derivative thereof, vitamin B5 or a derivative thereof, para-aminobenzoic acid (PABA), nicotinamide riboside (NR), hyaluronic acid, and biotin.

In one aspect, provided herein is a composition comprising nine or more of collagen, creatine or a derivative thereof, trans-resveratrol, vitamin C or a derivative thereof, coenzyme Q10 (CoQ10), spermidine, folate, or a derivative thereof, vitamin B12 or a derivative thereof, vitamin B5 or a derivative thereof, para-aminobenzoic acid (PABA), nicotinamide mononucleotide (NMN), hyaluronic acid, biotin, and a liquid solvent.

In one aspect, provided herein is a composition comprising nine or more of collagen, creatine or a derivative thereof, trans-resveratrol, vitamin C or a derivative thereof, coenzyme Q10 (CoQ10), spermidine, folate or a derivative thereof, vitamin B12, one or more precursors of NAD$^+$, hyaluronic acid, biotin, and a liquid solvent. In some aspects, the composition comprises from about 1 gram to about 25 grams of collagen. In some aspects, the composition comprises about 10 grams of collagen. In some aspects, the composition comprises from about 1 gram to about 15 grams of creatine or a derivative thereof. In some aspects, the composition comprises about 5 grams of creatine or a derivative thereof. In some aspects, the composition comprises from about 50 milligrams to about 5,000 milligrams of trans-resveratrol. In some aspects, the composition comprises about 500 milligrams of trans-resveratrol. In some aspects, the composition comprises from about 50 milligrams to about 2,000 milligrams of hyaluronic acid. In some aspects, the composition comprises about 250 milligrams of hyaluronic acid. In some aspects, the composition comprises from about 50 milligrams to about 1,000 milligrams of CoQ10. In some aspects, the composition comprises about 200 milligrams of CoQ10. In some aspects, the composition comprises from about 50 milligrams to about 5,000 milligrams of one or more precursors of NAD$^+$. In some aspects, the composition comprises about 500 milligrams of one or more precursors of NAD$^+$. In some aspects, the composition comprises from about 50 milligrams to about 5,000 milligrams of NMN. In some aspects, the composition comprises about 500 milligrams of NMN. In some aspects, the composition comprises from about 50 milligrams to about 5,000 milligrams of NR. In some aspects, the composition comprises about 500 milligrams of NR. In some aspects, the composition comprises from about 1 milligram to about 1,000 milligrams of spermidine. In some aspects, the composition comprises about 10 milligrams of spermidine. In some aspects, the composition comprises from about 100 milligrams to about 2,000 milligrams of vitamin C. In some aspects, the composition comprises about 500 milligrams of vitamin C. In some aspects, the composition comprises from about 5 micrograms to about 25,000 micrograms of biotin. In some aspects, the composition comprises about 2,500 micrograms of biotin. In some aspects, the composition comprises from about 5 micrograms to about 10,000 micrograms of folate. In some aspects, the composition comprises about 1,000 micrograms of folate. In some aspects, the composition comprises from about 5 micrograms to about 10,000 micrograms of folic acid. In some aspects, the composition comprises about 1,000 micrograms of folic acid. In some aspects, the composition comprises from about 5 micrograms to about 1,000 micrograms of vitamin B12. In some aspects, the composition comprises about 100 micrograms of vitamin B12. In some aspects, the composition comprises about 10 milligrams to about 5,000 milligrams of vitamin B5. In some aspects, the composition comprises about 500 milligrams of vitamin B5. In some aspects, the composition comprises about 10 milligrams to about 5,000 milligrams of para-aminobenzoic acid (PABA). In some aspects, the composition comprises about 500 milligrams of PABA. In some aspects, the vitamin B5 is present in the composition in the form of pantothenic acid, D-calcium pantothenate, pantethine, or a combination thereof. In some aspects, the composition further comprises a liquid solvent. In some aspects, the liquid solvent comprises one or more of water, an animal-based milk, or a plant-based milk. In some instances, the plant-based milk is selected from the group consisting of soy milk, almond milk, oat milk, pea milk, rice milk, coconut milk, and macadamia nut milk.

In one aspect, provided herein is a composition comprising eight or more of about 1 gram to about 25 grams of collagen, about 1 gram to about 15 grams of creatine or a derivative thereof, about 100 milligrams to about 2,000 milligrams of trans-resveratrol, about 100 milligrams to about 2,000 milligrams of vitamin C, about 50 milligrams to about 1,000 milligrams of CoQ10, about 1 milligram to about 1,000 milligrams of spermidine, about 5 micrograms to about 5,000 micrograms of folate or a derivative thereof, about 2 micrograms to about 1,000 micrograms of vitamin B12 or a derivative thereof, about 10 milligrams to about 5,000 milligrams of vitamin B5, about 10 milligrams to about 5,000 milligrams of para-aminobenzoic acid (PABA), about 50 milligrams to about 5,000 milligrams of one or more precursors of NAD⁺, about 50 milligrams to about 1,000 milligrams of hyaluronic acid, and about 5 micrograms to about 25,000 micrograms of biotin. In some aspects, the composition comprises about 10 grams of collagen. The composition of any one of claim 1, wherein the composition comprises about 5 grams of creatine or a derivative thereof. In some aspects, the composition comprises about 500 milligrams of trans-resveratrol. In some aspects, the composition comprises about 250 milligrams of hyaluronic acid. In some aspects, the composition comprises about 200 milligrams of CoQ10. In some aspects, the composition comprises about 500 milligrams of the one or more precursors of NAD⁺. In some aspects, the one or more precursors of NAD+ is/are selected from the group consisting of nicotinamide, NR, NMN, and niacin. In some aspects, the composition comprises about 10 milligrams of spermidine. In some aspects, the composition comprises about 500 milligrams of vitamin C or a derivative thereof. In some aspects, the composition comprises about 2,500 micrograms of biotin. In some aspects, the composition comprises about 1,000 micrograms of folate or a derivative thereof. In some aspects, the composition comprises about 100 micrograms of vitamin B12 or a derivative thereof. In some aspects, the composition comprises about 500 milligrams of vitamin B5. In some aspects, the vitamin B5 is present in the composition in the form of pantothenic acid, D-calcium pantothenate, pantethine, or a combination thereof. In some aspects, the composition comprises about 500 milligrams of para-aminobenzoic acid (PABA). In some aspects, the composition further comprises a liquid solvent. In some aspects, the liquid solvent comprises one or more of water, an animal-based milk, a plant-based milk, or a combination thereof. In some aspects, the plant-based milk is selected from the group consisting of soy milk, almond milk, oat milk, pea milk, rice milk, coconut milk, and macadamia nut milk. In some aspects, the composition further comprises one or more additive ingredients selected from the group consisting of flavoring agents, sweetening agents, and preservatives. In some aspects, the composition further comprises one or more sweetening agents selected from the group consisting of sucralose, stevia, aspartame, acesulfame potassium, xylitol, and erythritol. In some aspects, the composition further comprises one or more flavoring agents selected from the group consisting of natural flavors, artificial flavors, cocoa powder, vanillin, citric acid, maltodextrin, a flavonoid, and a flavanol. In some aspects, the composition further comprises one or more sources of dietary protein. In some aspects, the composition comprises from about 1 gram to about 50 grams of the one or more sources of dietary protein. In some aspects, the composition comprises about 20 grams of the one or more sources of dietary protein. In some aspects, the one or more sources of dietary protein is an animal-based protein source, a plant-based protein source, or a combination thereof. In some aspects, the one or more sources of dietary protein is whey protein isolate. In some aspects, the composition is formulated as a powdered composition. In some aspects, the composition is formulated as a powdered composition. In some aspects, provided herein is a method of promoting longevity in a human subject in need thereof, comprising administering the composition to the human subject, wherein the composition is combined with about 8 fluid ounces to about 16 fluid ounces of a liquid solvent to form a liquid composition, wherein the administering is achieved via oral ingestion of the liquid composition. In some aspects, the administering is once daily.

In one aspect, provided herein is a composition consisting essentially of one or more antioxidants, one or more vitamins or vitamin complexes thereof, one or more polysaccharides, one or more precursors of nicotinamide adenine dinucleotide (NAD⁺), one or more amino acid derivatives, and one or more polyamines. In some instances, the one or more antioxidants is selected from the group consisting of vitamin C, trans-resveratrol, CoQ10, zinc, tocopherols, tocotrienols, beta-carotene, selenium, lutein, zeaxanthin, a flavonoid, and flavonoid, and a polyphenol. In some instances, the one or more vitamins or vitamin complexes thereof is selected from the group consisting of vitamin A, one or more B-vitamins, a vitamin B complex, vitamin C, vitamin D, vitamin E, and vitamin K, or one or more derivatives thereof. In some instances, the one or more vitamins or vitamin complexes thereof is selected from the group consisting of retinol and derivatives thereof, carotenoids, thiamine, riboflavin, niacin, pyridoxine, folate, folic acid, cobalamin, an ascorbic acid, a mineral ascorbate, liposomal vitamin C, ergocalciferol, cholecalciferol, tocopherol, and derivatives thereof, phylloquinone, pantothenic acid, and menaquinone. In some instances, the mineral ascorbate is selected from the group consisting of sodium ascorbate, calcium ascorbate, and magnesium ascorbate. In some instances, the one or more polysaccharides is selected from the group consisting of hyaluronic acid, beta-glucans, inulin, psyllium husk, pectin, chitosan, and glucomannan. In some instances, the one or more precursors of NAD⁺ is selected from the group consisting of nicotinamide, NR, NMN, and niacin. In some instances, the one or more amino acid derivatives is selected from the group consisting of creatine, carnitine, taurine, glutathione, glycine, arginine, or derivatives thereof. In some instances, the one or more polyamines is selected from the group consisting of spermidine and spermine. In some instances, the composition further comprises a liquid solvent. In some instances, the liquid solvent comprises one or more of water, an animal-based milk, or a plant-based milk. In some instances, the plant-based milk is selected from the group consisting of soy milk, almond milk, oat milk, pea milk, rice milk, coconut milk, and macadamia nut milk. In some instances, the composition further comprises one or more sweetening agents. In some instances, the one or more sweetening agents is selected from the group consisting of sucralose, stevia, aspartame, acesulfame potassium, xylitol, and erythritol. In some instances, the composition further comprises one or more flavoring agents. In some instances, the one or more flavoring agents is selected from the group consisting of natural flavors, artificial flavors, cocoa powder, vanillin, citric acid, maltodextrin, a flavonoid, and a flavanol. In some cases, the flavonoid is a flavanol. In some instances, the composition further comprises a source of dietary protein. In some aspects, the composition comprises from about 1 gram to about 50 grams of the source of dietary protein. In some aspects, the composition comprises about 20 grams of the source of dietary protein. In some aspects, the source of dietary protein is an animal-based protein source, a plant-based protein source, or a combination thereof. In some instances, the protein source is whey protein isolate. In some aspects, the composition comprises one or more sources of dietary fiber. In some aspects, the composition comprises from about 3 grams to about 50 grams of dietary fiber. In some aspects, the composition comprises about 5 grams of dietary fiber.

In one aspect, provided herein is a method comprising administering to a human subject a composition disclosed herein. In some aspects, the composition is formulated as a powdered composition. In some instances, the administering further comprises dissolving the powdered composition into a liquid solvent, wherein upon dissolution of the composition forms a liquid composition. In some cases, the liquid solvent comprises one or more of: water, an animal-based milk, or a plant-based milk. In another aspect, the plant-based milk is selected from the group consisting of soy milk, almond milk, cashew milk, oat milk, pea milk, rice milk, coconut milk, and macadamia nut milk. In some instances, the administering comprises the dissolution of at least 35 grams of the powdered composition into the liquid solvent. In some instances, the administering comprises dissolution of about 40 grams of the powdered composition into the liquid solvent. In some instances, the administering comprises dissolution of the powdered composition into at least 8 fluid ounces of the liquid solvent. In another aspect, the administering comprises dissolution of the powdered composition into from about 8 fluid ounces to about 16 fluid ounces of the liquid solvent. In some aspects, the administering occurs at least once daily. In some aspects, the administering promotes elasticity and hydration of skin and connective tissues in the human subject. In some aspects, the administering improves metabolic function in the human subject. In some instances, the improved metabolic function is selected from the group consisting of cellular energy production, modulation of blood glucose, and modulation of hormones associated with weight management. In some aspects, the administering promotes improved cognitive function in the human subject. In some aspects, the administering promotes muscle growth and/or repair in the human subject. In some aspects, the administering prolongs muscle endurance in the human subject. In some aspects, the administering improves cardiovascular function in the human subject. In some aspects, the administering delays onset of aging in the human subject. In some aspects, the administering induces improved immune function in the human subject. In some cases, the human subject is a male. In some cases, the human subject is a female. In some instances, the human subject is at least 40 years of age. In some instances, the human subject is at least 50 years of age. In some aspects, the human subject suffers from one or more gastrointestinal conditions. In some instances, the powdered composition is administered in the form of single-serving satchels. In some instances, the powdered composition is in the form of a multi-serving cannister prior to the administering. In some instances, the liquid composition is in the form of a pre-mixed beverage prior to the administering. In some cases, the liquid composition requires refrigeration prior to the administering. In some aspects, one or more components of the composition is in an amount sufficient to have an identical or greater health outcome relative to an oral supplement comprising the one or more components as the sole active ingredient(s). In some instances, the oral supplement is a tablet or oral capsule comprising the one or more components and one or more pharmaceutically acceptable excipients, binders, fillers, or a combination thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

In some instances, the compositions provided herein are suitable for consumption by aging populations (e.g., at least 40 years of age) in order to supplement various nutritional needs in addition to nutrients supplied by diet. As humans age, the body's ability to absorb and utilize nutrients from food may decline, despite progressively increasing nutrient needs. Furthermore, the biological processes that protect against cellular damage, support immune function, and maintain the health of the heart, skin, and brain often become less efficient. Simultaneously, various nutrients and functional compounds, including, but not limited to, $NAD^+$, vitamins (e.g., B-vitamins, vitamin C, vitamin A, etc.), are commonly deficient in older adults, which can contribute to various health concerns, which can include accelerated aging, cognitive decline, reduced cardiovascular function, reduced metabolic function, reduced immune function, and declining integrity of hair, skin, and joints. Other compounds, like omega-3 fatty acids and antioxidant vitamins, can help to support heart and brain health. $NAD^+$ precursors and certain polyphenols, which, may confer certain anti-aging properties, can potentially serve to counteract one or more of the cellular changes that can occur with aging. As such, dietary supplementation in adults with a targeted selection of nutrients and functional compounds can respond to the cellular changes that can occur with aging and optimize levels of vital nutrients to support optimal health and longevity.

In some embodiments, disclosed herein are compositions (e.g., nutritional supplements) for the promotion of longevity and overall wellness. Example compositions provided herein comprise various nutrients and functional compounds which may target multiple facets of health including but not limited to, muscle growth and recovery, muscle endurance, antioxidant capabilities, skin, hair, and joint health, as well as cellular and cardiovascular functionality. In some aspects, the compositions and formulations presented herein promote health and longevity in an individual. The compositions disclosed herein may be suitable for efficient absorption of one or more active ingredients in the composition. Example compositions comprise a variety of nutrients and functional compounds, including, but not limited to collagen, creatine, trans-resveratrol, vitamin C, hyaluronic acid, biotin, CoQ10, spermidine, folate, vitamin B12, $NAD^+$ precursors, and one or more sources of dietary protein. In some instances, the compositions provided herein contribute to various health markers, such as muscle health, antioxidant function, skin, hair and joint health, cellular and cardiovascular health, and overall vitality. In some aspects, provided herein is a composition comprising one or more antioxidants; one or more vitamins or vitamin complexes thereof, one or more polysaccharides, one or more precursors of nicotinamide adenine dinucleotide ($NAD^+$), one or more proteins or amino acid derivatives, and one or more polyamines. In one aspect, provided is a composition comprising whey protein isolate, collagen, creatine, trans-resveratrol, vitamin C, hyaluronic acid, biotin, CoQ10, spermidine, folate, Vitamin B12, and $NAD^+$ precursors. In some embodiments, the quantities of these components can vary within predefined ranges based on the specific need and health status of the individual consuming the composition.

Certain embodiments provide a composition comprising various nutrients and one or more additional components to enhance the bioavailability and effectiveness of said nutrients. The compositions disclosed herein may further comprise additional ingredients such as sweeteners, flavoring agents, and other natural supplements. Further embodiments provide a method for using the compositions described herein.

The details of one or more inventive embodiments are set forth in the accompanying claims and the description herein. Other features, objects, and advantages of the inventive embodiments disclosed and contemplated herein can be combined with any other embodiment unless explicitly excluded.

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range, e.g., ±15% of a referenced numeral value. About also includes the exact amount, for example "about 5 grams" means "about 5 grams" and also "5 grams." Generally, the term "about" includes an amount that would be expected to be within experimental error.

In some embodiments, the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

In some embodiments, the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

Administration and subsequent uptake (e.g., absorption) of compositions, nutrients, and/or functional compounds disclosed herein, for example and not by way of limitation, is achieved by ingestion of the composition in various forms that may include a powdered composition, a powdered composition dissolved in a liquid solvent suitable for consumption, a powdered composition accompanied by or in combination with a food and/or a beverage.

As used herein, the term "nutritional supplement" refers to a product intended to provide nutrients in addition to existing (e.g., deficient, or absent) quantities from diet alone. These nutrients can include, but are not limited to, vitamins, minerals, fiber, fatty acids, or amino acids. Nutritional supplements can be delivered in various forms such as tablets, capsules, powders, gels, liquids, or gummies. Consumption of nutritional supplements may serve to complement the diet and promote overall health and wellbeing, augment nutrient intake, support specific health goals, and/or address specific dietary needs or deficiencies.

As used herein, the term "liquid solvent" refers to any substance, naturally occurring or synthetic, that can dissolve a composition described herein and yield a solution suitable for human consumption. Examples of suitable liquid solvents include but are not limited to water, an animal-based milk, a plant-based milk, or a combination thereof. The choice of the liquid solvent can be tailored according to individual dietary needs, preferences, or the intended mode of administration.

As used herein, the term "vitamin" refers to a group of organic compounds considered essential in small quantities for normal human physiological function. Vitamins may encompass a variety of forms and can be found in multiple states, such as precursors or derivatives. For example, vitamin C can be found in the form of ascorbic acid, ascorbyl palmitate, a mineral ascorbate (e.g., sodium ascorbate, calcium ascorbate, and magnesium ascorbate, etc). In another instance, vitamin D can exist in several forms, such as cholecalciferol (vitamin D3) and ergocalciferol (vitamin D2). Other vitamins, such as those in the B complex group may exist as several different "vitamers" or forms. For instance, vitamin B may occur as including B1 (thiamine), B2 (riboflavin), B3 (niacin and niacinamide), B5 (pantothenic acid), B6 (pyridoxine, pyridoxal, and pyridoxamine), B7 (biotin), B9 (folic acid and folate), and B12 (cobalamins such as cyanocobalamin, methylcobalamin, and hydroxocobalamin). Non-limiting examples of vitamin E may include tocopherols (alpha, beta, gamma, and delta) and tocotrienols (alpha, beta, gamma, and delta). In some embodiments, vitamin A includes preformed vitamin A, or retinoids (e.g., retinol, retinal, and retinoic acid, etc), and provitamin A carotenoids (e.g., beta-carotene). Vitamins may, in some aspects, be referred to as being fat-soluble vitamins (e.g., vitamins A, D, E, K, etc). or water-soluble vitamins (e.g., B-complex vitamins and vitamin C, etc).

The section headings used herein are for organizational purposes only and are not to be construed as limiting the subject matter described.

Cellular Growth, Repair and Metabolic Function

In one aspect, the compositions provided herein comprise components that play an integral role in modulating cellular energy production and metabolic processes. In some instances, the compositions provided herein improve cellular function and energy availability. In some cases, modulation of cellular energy production and metabolic processes can be accomplished by supplementing dietary intake of various amino acid derivatives. Non-limiting examples of amino acid derivatives include creatine, carnitine, taurine, glutathione, glycine, and arginine.

Creatine

In some embodiments, the compositions provided herein comprise creatine or a derivative thereof, a compound with various applications including, but not limited to, energy production in muscle cells. Creatine is an amino acid derivative that is naturally synthesized in the human body, predominantly in the liver and kidney, and is transported to muscles where it is converted into creatine phosphate, a high-energy metabolite used to generate ATP, the primary source of energy for muscle contraction. Creatine supplementation, as contemplated in the present disclosure, can enhance physical performance by increasing the availability of immediate energy in muscle tissue, for example, during short-term, high-intensity exercise. Non-limiting examples of creatine forms include creatine monohydrate, creatine ethyl ester, creatine malate, creatine citrate, and buffered creatine. In some embodiments, creatine supplementation promotes increases in muscle mass, strength, and overall exercise performance.

In some embodiments, the composition comprises about 1 gram of creatine to about 15 grams of creatine. In some embodiments, the composition comprises about 1 gram of creatine to about 2 grams of creatine, about 1 gram of creatine to about 3 grams of creatine, about 1 gram of creatine to about 4 grams of creatine, about 1 gram of creatine to about 5 grams of creatine, about 1 gram of creatine to about 6 grams of creatine, about 1 gram of creatine to about 7 grams of creatine, about 1 gram of creatine to about 8 grams of creatine, about 1 gram of creatine to about 9 grams of creatine, about 1 gram of creatine to about 10 grams of creatine, about 1 gram of creatine to about 15 grams of creatine, about 2 grams of creatine to about 3 grams of creatine, about 2 grams of creatine to about 4 grams of creatine, about 2 grams of creatine to about 5 grams of creatine, about 2 grams of creatine to about 6 grams of creatine, about 2 grams of creatine to about 7 grams of creatine, about 2 grams of creatine to about 8 grams of creatine, about 2 grams of creatine to about 9 grams of creatine, about 2 grams of creatine to about 10 grams of creatine, about 2 grams of creatine to about 15 grams of creatine, about 3 grams of creatine to about 4 grams of creatine, about 3 grams of creatine to about 5 grams of creatine, about 3 grams of creatine to about 6 grams of creatine, about 3 grams of creatine to about 7 grams of creatine, about 3 grams of creatine to about 8 grams of creatine, about 3 grams of creatine to about 9 grams of creatine, about 3 grams of creatine to about 10 grams of creatine, about 3 grams of creatine to about 15 grams of creatine, about 4 grams of creatine to about 5 grams of creatine, about 4 grams of creatine to about 6 grams of creatine, about 4 grams of creatine to about 7 grams of creatine, about 4 grams of creatine to about 8 grams of creatine, about 4 grams of creatine to about 9 grams of creatine, about 4 grams of creatine to about 10 grams of creatine, about 4 grams of creatine to about 15 grams of creatine, about 5 grams of creatine to about 6 grams of creatine, about 5 grams of creatine to about 7 grams of creatine, about 5 grams of creatine to about 8 grams of creatine, about 5 grams of creatine to about 9 grams of creatine, about 5 grams of creatine to about 10 grams of creatine, about 5 grams of creatine to about 15 grams of creatine, about 6 grams of creatine to about 7 grams of creatine, about 6 grams of creatine to about 8 grams of creatine, about 6 grams of creatine to about 9 grams of creatine, about 6 grams of creatine to about 10 grams of creatine, about 6 grams of creatine to about 15 grams of creatine, about 7 grams of creatine to about 8 grams of creatine, about 7 grams of creatine to about 9 grams of creatine, about 7 grams of creatine to about 10 grams of creatine, about 7 grams of creatine to about 15 grams of creatine, about 8 grams of creatine to about 9 grams of creatine, about 8 grams of creatine to about 10 grams of creatine, about 8 grams of creatine to about 15 grams of creatine, about 9 grams of creatine to about 10 grams of creatine, about 9 grams of creatine to about 15 grams of creatine, or about 10 grams of creatine to about 15 grams of creatine. In some embodiments, the composition comprises about 1 gram of creatine, about 2 grams of creatine, about 3 grams of creatine, about 4 grams of creatine, about 5 grams of creatine, about 6 grams of creatine, about 7 grams of creatine, about 8 grams of creatine, about 9 grams of creatine, about 10 grams of creatine, or about 15 grams of creatine. In some embodiments, the composition comprises at least about 1 gram of creatine, about 2 grams of creatine, about 3 grams of creatine, about 4 grams of creatine, about 5 grams of creatine, about 6 grams of creatine, about 7 grams of creatine, about 8 grams of creatine, about 9 grams of creatine, or about 10 grams of creatine. In some embodiments, the composition comprises at most about 2 grams of creatine, about 3 grams of creatine, about 4 grams of creatine, about 5 grams of creatine, about 6 grams of creatine, about 7 grams of creatine, about 8 grams of creatine, about 9 grams of creatine, about 10 grams of creatine, or about 15 grams of creatine.

Precursors of NAD⁺

In some embodiments, the compositions of the present disclosure incorporate one or more precursors of $NAD^+$, encompassing compounds that can be converted into $NAD^+$ in the human body. In some instances, precursors of $NAD^+$ include nicotinamide mononucleotide (NMN), nicotinamide riboside (NR), nicotinamide, and niacin. $NAD^+$, or Nicotinamide adenine dinucleotide, is a coenzyme found in all living cells and has fundamental roles in metabolic processes and energy production. However, levels of $NAD^+$ may decline with age, which can lead to a variety of health issues including, but not limited to, metabolic diseases, neurodegenerative diseases, accelerated aging and age-related health issues (e.g., reduced organ function, decreased insulin sensitivity, loss of muscle mass, cognitive decline, etc.), cardiovascular diseases, impaired DNA repair mechanisms, and chronic inflammation. Supplementation with $NAD^+$ precursors may contribute to replenishment the body's supply of $NAD^+$ and subsequent downstream effects including but not limited to maintenance of or improvements in cellular energy production, DNA repair mechanisms, and cognitive function.

In some embodiments, the composition comprises about 50 milligrams of NR to about 5,000 milligrams of NR. In some embodiments, the composition comprises about 50 milligrams of NR to about 100 milligrams of NR, about 50 milligrams of NR to about 200 milligrams of NR, about 50 milligrams of NR to about 300 milligrams of NR, about 50 milligrams of NR to about 400 milligrams of NR, about 50 milligrams of NR to about 500 milligrams of NR, about 50 milligrams of NR to about 1,000 milligrams of NR, about 50 milligrams of NR to about 2,000 milligrams of NR, about 50 milligrams of NR to about 3,000 milligrams of NR, about 50 milligrams of NR to about 4,000 milligrams of NR, about 50 milligrams of NR to about 5,000 milligrams of NR, about 100 milligrams of NR to about 200 milligrams of NR, about 100 milligrams of NR to about 300 milligrams of NR, about 100 milligrams of NR to about 400 milligrams of NR, about 100 milligrams of NR to about 500 milligrams of NR, about 100 milligrams of NR to about 1,000 milligrams of NR, about 100 milligrams of NR to about 2,000 milligrams of NR, about 100 milligrams of NR to about 3,000 milligrams of NR, about 100 milligrams of NR to about 4,000 milligrams of NR, about 100 milligrams of NR to about 5,000 milligrams of NR, about 200 milligrams of NR to about 300 milligrams of NR, about 200 milligrams of NR to about 400 milligrams of NR, about 200 milligrams of NR to about 500 milligrams of NR, about 200 milligrams of NR to about 1,000 milligrams of NR, about 200 milligrams of NR to about 2,000 milligrams of NR, about 200 milligrams of NR to about 3,000 milligrams of NR, about 200 milligrams of NR to about 4,000 milligrams of NR, about 200 milligrams of NR to about 5,000 milligrams of NR, about 300 milligrams of NR to about 400 milligrams of NR, about 300 milligrams of NR to about 500 milligrams of NR, about 300 milligrams of NR to about 1,000 milligrams of NR, about 300 milligrams of NR to about 2,000 milligrams of NR, about 300 milligrams of NR to about 3,000 milligrams of NR, about 300 milligrams of NR to about 4,000 milligrams of NR, about 300 milligrams of NR to about 5,000 milligrams of NR, about 400 milligrams of NR to about 500 milligrams of NR, about 400 milligrams of NR to about 1,000 milligrams of NR, about 400 milligrams of NR to about 2,000 milligrams of NR, about 400 milligrams of NR to about 3,000 milligrams of NR, about 400 milligrams of NR to about 4,000 milligrams of NR, about 400 milligrams of NR to about 5,000 milligrams of NR, about 500 milligrams of NR to about 1,000 milligrams of NR, about 500 milligrams of NR to about 2,000 milligrams of NR, about 500 milligrams of NR to about 3,000 milligrams of NR, about 500 milligrams of NR to about 4,000 milligrams of NR, about 500 milligrams of NR to about 5,000 milligrams of NR, about 1,000 milligrams of NR to about 2,000 milligrams of NR, about 1,000 milligrams of NR to about 3,000 milligrams of NR, about 1,000 milligrams of NR to about 4,000 milligrams of NR, about 1,000 milligrams of NR to about 5,000 milligrams of NR, about 2,000 milligrams of NR to about 3,000 milligrams of NR, about 2,000 milligrams of NR to about 4,000 milligrams of NR, about 2,000 milligrams of NR to about 5,000 milligrams of NR, about 3,000 milligrams of NR to about 4,000 milligrams of NR, about 3,000 milligrams of NR to about 5,000 milligrams of NR, or about 4,000 milligrams of NR to about 5,000 milligrams of NR. In some embodiments, the composition comprises about 50 milligrams of NR, about 100 milligrams of NR, about 200 milligrams of NR, about 300 milligrams of NR, about 400 milligrams of NR, about 500 milligrams of NR, about 1,000 milligrams of NR, about 2,000 milligrams of NR, about 3,000 milligrams of NR, about 4,000 milligrams of NR, or about 5,000 milligrams of NR. In some embodiments, the composition comprises at least about 50 milligrams of NR, about 100 milligrams of NR, about 200 milligrams of NR, about 300 milligrams of NR, about 400 milligrams of NR, about 500 milligrams of NR, about 1,000 milligrams of NR, about 2,000 milligrams of NR, about 3,000 milligrams of NR, or about 4,000 milligrams of NR. In some embodiments, the composition comprises at most about 100 milligrams of NR, about 200 milligrams of NR, about 300 milligrams of NR, about 400 milligrams of NR, about 500 milligrams of NR, about 1,000 milligrams of NR, about 2,000 milligrams of NR, about 3,000 milligrams of NR, about 4,000 milligrams of NR, or about 5,000 milligrams of NR.

In some embodiments, the composition comprises about 50 milligrams of NMN to about 5,000 milligrams of NMN. In some embodiments, the composition comprises about 50 milligrams of NMN to about 100 milligrams of NMN, about 50 milligrams of NMN to about 200 milligrams of NMN, about 50 milligrams of NMN to about 300 milligrams of NMN, about 50 milligrams of NMN to about 400 milligrams of NMN, about 50 milligrams of NMN to about 500 milligrams of NMN, about 50 milligrams of NMN to about 1,000 milligrams of NMN, about 50 milligrams of NMN to about 2,000 milligrams of NMN, about 50 milligrams of NMN to about 3,000 milligrams of NMN, about 50 milligrams of NMN to about 4,000 milligrams of NMN, about 50 milligrams of NMN to about 5,000 milligrams of NMN, about 100 milligrams of NMN to about 200 milligrams of NMN, about 100 milligrams of NMN to about 300 milligrams of NMN, about 100 milligrams of NMN to about 400 milligrams of NMN, about 100 milligrams of NMN to about 500 milligrams of NMN, about 100 milligrams of NMN to about 1,000 milligrams of NMN, about 100 milligrams of NMN to about 2,000 milligrams of NMN, about 100 milligrams of NMN to about 3,000 milligrams of NMN, about 100 milligrams of NMN to about 4,000 milligrams of NMN, about 100 milligrams of NMN to about 5,000 milligrams of NMN, about 200 milligrams of NMN to about 300 milligrams of NMN, about 200 milligrams of NMN to about 400 milligrams of NMN, about 200 milligrams of NMN to about 500 milligrams of NMN, about 200 milligrams of NMN to about 1,000 milligrams of NMN, about 200 milligrams of NMN to about 2,000 milligrams of NMN, about 200 milligrams of NMN to about 3,000 milligrams of NMN, about 200 milligrams of NMN to about 4,000 milligrams of NMN, about 200 milligrams of NMN to about 5,000 milligrams of NMN, about 300 milligrams of NMN to about 400 milligrams of NMN, about 300 milligrams of NMN to about 500 milligrams of NMN, about 300 milligrams of NMN to about 1,000 milligrams of NMN, about 300 milligrams of NMN to about 2,000 milligrams of NMN, about 300 milligrams of NMN to about 3,000 milligrams of NMN, about 300 milligrams of NMN to about 4,000 milligrams of NMN, about 300 milligrams of NMN to about 5,000 milligrams of NMN, about 400 milligrams of NMN to about 500 milligrams of NMN, about 400 milligrams of NMN to about 1,000 milligrams of NMN, about 400 milligrams of NMN to about 2,000 milligrams of NMN, about 400 milligrams of NMN to about 3,000 milligrams of NMN, about 400 milligrams of NMN to about 4,000 milligrams of NMN, about 400 milligrams of NMN to about 5,000 milligrams of NMN, about 500 milligrams of NMN to about 1,000 milligrams of NMN, about 500 milligrams of NMN to about 2,000 milligrams of NMN, about 500 milligrams of NMN to about 3,000 milligrams of NMN, about 500 milligrams of NMN to about 4,000 milligrams of NMN, about 500 milligrams of NMN to about 5,000 milligrams of NMN, about 1,000 milligrams of NMN to about 2,000 milligrams of NMN, about 1,000 milligrams of NMN to about 3,000 milligrams of NMN, about 1,000 milligrams of NMN to about 4,000 milligrams of NMN, about 1,000 milligrams of NMN to about 5,000 milligrams of NMN, about 2,000 milligrams of NMN to about 3,000 milligrams of NMN, about 2,000 milligrams of NMN to about 4,000 milligrams of NMN, about 2,000 milligrams of NMN to about 5,000 milligrams of NMN, about 3,000 milligrams of NMN to about 4,000 milligrams of NMN, about 3,000 milligrams of NMN to about 5,000 milligrams of NMN, or about 4,000 milligrams of NMN to about 5,000 milligrams of NMN. In some embodiments, the composition comprises about 50 milligrams of NMN, about 100 milligrams of NMN, about 200 milligrams of NMN, about 300 milligrams of NMN, about 400 milligrams of NMN, about 500 milligrams of NMN, about 1,000 milligrams of NMN, about 2,000 milligrams of NMN, about 3,000 milligrams of NMN, about 4,000 milligrams of NMN, or about 5,000 milligrams of NMN. In some embodiments, the composition comprises at least about 50 milligrams of NMN, about 100 milligrams of NMN, about 200 milligrams of NMN, about 300 milligrams of NMN, about 400 milligrams of NMN, about 500 milligrams of NMN, about 1,000 milligrams of NMN, about 2,000 milligrams of NMN, about 3,000 milligrams of NMN, or about 4,000 milligrams of NMN. In some embodiments, the composition comprises at most about 100 milligrams of NMN, about 200 milligrams of NMN, about 300 milligrams of NMN, about 400 milligrams of NMN, about 500 milligrams of NMN, about 1,000 milligrams of NMN, about 2,000 milligrams of NMN, about 3,000 milligrams of NMN, about 4,000 milligrams of NMN, or about 5,000 milligrams of NMN.

In some embodiments, the composition comprises about 50 milligrams of one or more precursors of NAD$^+$ to about 5,000 milligrams of one or more precursors of NAD$^+$. In some embodiments, the composition comprises about 50 milligrams of one or more precursors of NAD$^+$ to about 100 milligrams of one or more precursors of NAD$^+$, about 50 milligrams of one or more precursors of NAD$^+$ to about 200 milligrams of one or more precursors of NAD$^+$, about 50 milligrams of one or more precursors of NAD$^+$ to about 300 milligrams of one or more precursors of NAD$^+$, about 50 milligrams of one or more precursors of NAD$^+$ to about 400 milligrams of one or more precursors of NAD$^+$, about 50 milligrams of one or more precursors of NAD$^+$ to about 500 milligrams of one or more precursors of NAD$^+$, about 50 milligrams of one or more precursors of NAD$^+$ to about 1,000 milligrams of one or more precursors of NAD$^+$, about 50 milligrams of one or more precursors of NAD$^+$ to about 2,000 milligrams of one or more precursors of NAD$^+$, about 50 milligrams of one or more precursors of NAD$^+$ to about 3,000 milligrams of one or more precursors of NAD$^+$, about 50 milligrams of one or more precursors of NAD$^+$ to about 4,000 milligrams of one or more precursors of NAD$^+$, about 50 milligrams of one or more precursors of NAD$^+$ to about 5,000 milligrams of one or more precursors of NAD$^+$, about 100 milligrams of one or more precursors of NAD$^+$ to about 200 milligrams of one or more precursors of NAD$^+$, about 100 milligrams of one or more precursors of NAD$^+$ to about 300 milligrams of one or more precursors of NAD$^+$, about 100 milligrams of one or more precursors of NAD$^+$ to about 400 milligrams of one or more precursors of NAD$^+$, about 100 milligrams of one or more precursors of NAD$^+$ to about 500 milligrams of one or more precursors of NAD$^+$, about 100 milligrams of one or more precursors of NAD$^+$ to about 1,000 milligrams of one or more precursors of NAD$^+$, about 100 milligrams of one or more precursors of NAD$^+$ to about 2,000 milligrams of one or more precursors of NAD$^+$, about 100 milligrams of one or more precursors of NAD$^+$ to about 3,000 milligrams of one or more precursors of NAD$^+$, about 100 milligrams of one or more precursors of NAD$^+$ to about 4,000 milligrams of one or more precursors of NAD$^+$, about 100 milligrams of one or more precursors of NAD$^+$ to about 5,000 milligrams of one or more precursors of NAD$^+$, about 200 milligrams of one or more precursors of NAD$^+$ to about 300 milligrams of one or more precursors of NAD$^+$, about 200 milligrams of one or more precursors of NAD$^+$ to about 400 milligrams of one or more precursors of NAD$^+$, about 200 milligrams of one or more precursors of NAD$^+$ to about 500 milligrams of one or more precursors of NAD$^+$, about 200 milligrams of one or more precursors of NAD$^+$ to about 1,000 milligrams of one or more precursors of NAD$^+$, about 200 milligrams of one or more precursors of NAD$^+$ to about 2,000 milligrams of one or more precursors of NAD$^+$, about 200 milligrams of one or more precursors of NAD$^+$ to about 3,000 milligrams of one or more precursors of NAD$^+$, about 200 milligrams of one or more precursors of NAD$^+$ to about 4,000 milligrams of one or more precursors of NAD$^+$, about 200 milligrams of one or more precursors of NAD$^+$ to about 5,000 milligrams of one or more precursors of NAD$^+$, about 300 milligrams of one or more precursors of NAD$^+$ to about 400 milligrams of one or more precursors of NAD$^+$, about 300 milligrams of one or more precursors of NAD$^+$ to about 500 milligrams of one or more precursors of NAD$^+$, about 300 milligrams of one or more precursors of NAD$^+$ to about 1,000 milligrams of one or more precursors of NAD$^+$, about 300 milligrams of one or more precursors of NAD$^+$ to about 2,000 milligrams of one or more precursors of NAD$^+$, about 300 milligrams of one or more precursors of NAD$^+$ to about 3,000 milligrams of one or more precursors of NAD$^+$, about 300 milligrams of one or more precursors of NAD$^+$ to about 4,000 milligrams of one or more precursors of NAD$^+$, about 300 milligrams of one or more precursors of NAD$^+$ to about 5,000 milligrams of one or more precursors of NAD$^+$, about 400 milligrams of one or more precursors of NAD$^+$ to about 500 milligrams of one or more precursors of NAD$^+$, about 400 milligrams of one or more precursors of NAD$^+$ to about 1,000 milligrams of one or more precursors of NAD$^+$, about 400 milligrams of one or more precursors of NAD$^+$ to about 2,000 milligrams of one or more precursors of NAD$^+$, about 400 milligrams of one or more precursors of NAD$^+$ to about 3,000 milligrams of one or more precursors of NAD$^+$, about 400 milligrams of one or more precursors of NAD$^+$ to about 4,000 milligrams of one or more precursors of NAD$^+$, about 400 milligrams of one or more precursors of NAD$^+$ to about 5,000 milligrams of one or more precursors of NAD$^+$, about 500 milligrams of one or more precursors of NAD$^+$ to about 1,000 milligrams of one or more precursors of NAD$^+$, about 500 milligrams of one or more precursors of NAD$^+$ to about 2,000 milligrams of one or more precursors of NAD$^+$, about 500 milligrams of one or more precursors of NAD$^+$ to about 3,000 milligrams of one or more precursors of NAD$^+$, about 500 milligrams of one or more precursors of NAD$^+$ to about 4,000 milligrams of one or more precursors of NAD$^+$, about 500 milligrams of one or more precursors of NAD$^+$ to about 5,000 milligrams of one or more precursors of NAD$^+$, about 1,000 milligrams of one or more precursors of NAD$^+$ to about 2,000 milligrams of one or more precursors of NAD$^+$, about 1,000 milligrams of one or more precursors of NAD$^+$ to about 3,000 milligrams of one or more precursors of NAD$^+$, about 1,000 milligrams of one or more precursors of NAD$^+$ to about 4,000 milligrams of one or more precursors of NAD$^+$, about 1,000 milligrams of one or more precursors of NAD$^+$ to about 5,000 milligrams of one or more precursors of NAD$^+$, about 2,000 milligrams of one or more precursors of NAD$^+$ to about 3,000 milligrams of one or more precursors of NAD$^+$, about 2,000 milligrams of one or more precursors of NAD$^+$ to about 4,000 milligrams of one or more precursors of NAD$^+$, about 2,000 milligrams of one or more precursors of NAD$^+$ to about 5,000 milligrams of one or more precursors of NAD$^+$, about 3,000 milligrams of one or more precursors of NAD$^+$ to about 4,000 milligrams of one or more precursors of NAD$^+$, about 3,000 milligrams of one or more precursors of NAD$^+$ to about 5,000 milligrams of one or more precursors of NAD$^+$, or about 4,000 milligrams of one or more precursors of NAD$^+$ to about 5,000 milligrams of one or more precursors of NAD$^+$. In some embodiments, the composition comprises about 50 milligrams of one or more precursors of NAD$^+$, about 100 milligrams of one or more precursors of NAD$^+$, about 200 milligrams of one or more precursors of NAD$^+$, about 300 milligrams of one or more precursors of NAD$^+$, about 400 milligrams of one or more precursors of NAD$^+$, about 500 milligrams of one or more precursors of NAD$^+$, about 1,000 milligrams of one or more precursors of NAD$^+$, about 2,000 milligrams of one or more precursors of NAD$^+$, about 3,000 milligrams of one or more precursors of NAD$^+$, about 4,000 milligrams of one or more precursors of NAD$^+$, or about 5,000 milligrams of one or more precursors of NAD$^+$. In some embodiments, the composition comprises at least about 50 milligrams of one or more precursors of NAD$^+$, about 100 milligrams of one or more precursors of NAD$^+$, about 200 milligrams of one or more precursors of NAD$^+$, about 300 milligrams of one or more precursors of NAD⁺,
about 400 milligrams of one or more precursors of NAD⁺,
about 500 milligrams of one or more precursors of NAD⁺,
about 1,000 milligrams of one or more precursors of NAD⁺,
about 2,000 milligrams of one or more precursors of NAD⁺,
about 3,000 milligrams of one or more precursors of NAD⁺,
or about 4,000 milligrams of one or more precursors of
NAD⁺. In some embodiments, the composition comprises at
most about 100 milligrams of one or more precursors of
NAD⁺, about 200 milligrams of one or more precursors of
NAD⁺, about 300 milligrams of one or more precursors of
NAD⁺, about 400 milligrams of one or more precursors of
NAD⁺, about 500 milligrams of one or more precursors of
NAD⁺, about 1,000 milligrams of one or more precursors of
NAD⁺, about 2,000 milligrams of one or more precursors of
NAD⁺, about 3,000 milligrams of one or more precursors of
NAD⁺, about 4,000 milligrams of one or more precursors of
NAD⁺, or about 5,000 milligrams of one or more precursors
of NAD⁺.

Spermidine

The compositions herein may comprise one or more
polyamines. Polyamines, including spermidine and/or sper-
mine, are organic compounds having two or more primary
amine groups, are naturally present in all living organisms
and are involved in numerous cellular processes. In some
instances, polyamines play a role in cell growth, prolifera-
tion, differentiation, and apoptosis. Spermidine, in particu-
lar, is a triamine that is useful in a variety of applications
including, but not limited to, stimulation of autophagy (e.g.,
removal of damaged proteins and organelles), which may
confer the effect of delayed cellular aging. In additional
aspects, spermidine may contribute to improved cardiovas-
cular health, enhanced immune function, and promotion of
hair growth. The body's ability to produce spermidine may
decrease with age. In some embodiments, supplementation
with spermidine can help maintain its optimal levels, and
may contribute to longevity, improved cardiovascular
health, and improved overall cellular function.

In some embodiments, the composition comprises sper-
midine in the amount of about 1 milligram to about 1,000
milligrams. In some embodiments, the composition com-
prises spermidine in the amount of about 1 milligram to
about 5 milligrams, about 1 milligram to about 10 milli-
grams, about 1 milligram to about 11 milligrams, about 1
milligram to about 12 milligrams, about 1 milligram to about
13 milligrams, about 1 milligram to about 14 milligrams,
about 1 milligram to about 15 milligrams, about 1 milligram
to about 25 milligrams, about 1 milligram to about 50
milligrams, about 1 milligram to about 100 milligrams,
about 1 milligram to about 1,000 milligrams, about 5
milligrams to about 10 milligrams, about 5 milligrams to
about 11 milligrams, about 5 milligrams to about 12 milli-
grams, about 5 milligrams to about 13 milligrams, about 5
milligrams to about 14 milligrams, about 5 milligrams to
about 15 milligrams, about 5 milligrams to about 25 milli-
grams, about 5 milligrams to about 50 milligrams, about 5
milligrams to about 100 milligrams, about 5 milligrams to
about 1,000 milligrams, about 10 milligrams to about 11
milligrams, about 10 milligrams to about 12 milligrams,
about 10 milligrams to about 13 milligrams, about 10
milligrams to about 14 milligrams, about 10 milligrams to
about 15 milligrams, about 10 milligrams to about 25
milligrams, about 10 milligrams to about 50 milligrams,
about 10 milligrams to about 100 milligrams, about 10
milligrams to about 1,000 milligrams, about 11 milligrams
to about 12 milligrams, about 11 milligrams to about 13
milligrams, about 11 milligrams to about 14 milligrams, about 11 milligrams to about 15 milligrams, about 11
milligrams to about 25 milligrams, about 11 milligrams to
about 50 milligrams, about 11 milligrams to about 100
milligrams, about 11 milligrams to about 1,000 milligrams,
about 12 milligrams to about 13 milligrams, about 12
milligrams to about 14 milligrams, about 12 milligrams to
about 15 milligrams, about 12 milligrams to about 25
milligrams, about 12 milligrams to about 50 milligrams,
about 12 milligrams to about 100 milligrams, about 12
milligrams to about 1,000 milligrams, about 13 milligrams
to about 14 milligrams, about 13 milligrams to about 15
milligrams, about 13 milligrams to about 25 milligrams,
about 13 milligrams to about 50 milligrams, about 13
milligrams to about 100 milligrams, about 13 milligrams to
about 1,000 milligrams, about 14 milligrams to about 15
milligrams, about 14 milligrams to about 25 milligrams,
about 14 milligrams to about 50 milligrams, about 14
milligrams to about 100 milligrams, about 14 milligrams to
about 1,000 milligrams, about 15 milligrams to about 25
milligrams, about 15 milligrams to about 50 milligrams,
about 15 milligrams to about 100 milligrams, about 15
milligrams to about 1,000 milligrams, about 25 milligrams
to about 50 milligrams, about 25 milligrams to about 100
milligrams, about 25 milligrams to about 1,000 milligrams,
about 50 milligrams to about 100 milligrams, about 50
milligrams to about 1,000 milligrams, or about 100 milli-
grams to about 1,000 milligrams. In some embodiments, the
composition comprises spermidine in the amount of about 1
milligram, about 5 milligrams, about 10 milligrams, about
11 milligrams, about 12 milligrams, about 13 milligrams,
about 14 milligrams, about 15 milligrams, about 25 milli-
grams, about 50 milligrams, about 100 milligrams, or about
1,000 milligrams. In some embodiments, the composition
comprises spermidine in the amount of at least about 1
milligram, about 5 milligrams, about 10 milligrams, about
11 milligrams, about 12 milligrams, about 13 milligrams,
about 14 milligrams, about 15 milligrams, about 25 milli-
grams, about 50 milligrams, or about 100 milligrams. In
some embodiments, the composition comprises spermidine
in the amount of at most about 5 milligrams, about 10
milligrams, about 11 milligrams, about 12 milligrams, about
13 milligrams, about 14 milligrams, about 15 milligrams,
about 25 milligrams, about 50 milligrams, about 100 milli-
grams, or about 1,000 milligrams.

Dietary Protein

The compositions disclosed herein may incorporate
dietary proteins, which supply essential amino acids that the
body cannot synthesize on its own. These amino acids play
a crucial role in promoting muscle protein synthesis (MPS),
thus aiding in counteracting the natural muscle loss, or
sarcopenia, associated with aging. Besides their role in
muscle health, dietary proteins are known to influence
hormones that regulate hunger and fullness. Specifically,
protein-rich meals can suppress ghrelin, a hormone that
signals hunger to the brain, and stimulate the release of
hormones like peptide YY and cholecystokinin, which pro-
mote feelings of fullness or satiety. This can contribute to
healthy weight management and overall metabolic health.
Sources of dietary protein, as contemplated in the compo-
sitions disclosed herein, can constitute dietary protein
sources in various forms, one or more of which may cater to
different dietary needs and preferences. These may incor-
porate protein from various sources including, but not lim-
ited to, protein concentrates, isolates, or hydrolysates. For
instance, sources of protein may comprise animal-based
proteins such as whey protein, casein proteins, or egg
protein. Alternatively, plant-based proteins, including, but not limited to, soy, pea, or brown rice proteins, can serve as suitable alternatives for individuals adhering to a plant-based diet or those with certain food sensitivities. Aging, in some instances, may have associations with a decrease in the body's efficiency in utilizing protein for MPS, potentially necessitating increased protein intake. Therefore, dietary protein supplementation could be especially beneficial for aging adults, both for supporting muscle health and promoting feelings of fullness through the modulation of hunger and satiety hormones, thus contributing to overall health and well-being.

In some embodiments, the composition comprises a source of dietary protein in the amount of about 1 gram to about 60 grams. In some embodiments, the composition comprises a source of dietary protein in the amount of about 1 gram to about 5 grams, about 1 gram to about 10 grams, about 1 gram to about 15 grams, about 1 gram to about 20 grams, about 1 gram to about 25 grams, about 1 gram to about 30 grams, about 1 gram to about 35 grams, about 1 gram to about 40 grams, about 1 gram to about 45 grams, about 1 gram to about 50 grams, about 1 gram to about 60 grams, about 5 grams to about 10 grams, about 5 grams to about 15 grams, about 5 grams to about 20 grams, about 5 grams to about 25 grams, about 5 grams to about 30 grams, about 5 grams to about 35 grams, about 5 grams to about 40 grams, about 5 grams to about 45 grams, about 5 grams to about 50 grams, about 5 grams to about 60 grams, about 10 grams to about 15 grams, about 10 grams to about 20 grams, about 10 grams to about 25 grams, about 10 grams to about 30 grams, about 10 grams to about 35 grams, about 10 grams to about 40 grams, about 10 grams to about 45 grams, about 10 grams to about 50 grams, about 10 grams to about 60 grams, about 15 grams to about 20 grams, about 15 grams to about 25 grams, about 15 grams to about 30 grams, about 15 grams to about 35 grams, about 15 grams to about 40 grams, about 15 grams to about 45 grams, about 15 grams to about 50 grams, about 15 grams to about 60 grams, about 20 grams to about 25 grams, about 20 grams to about 30 grams, about 20 grams to about 35 grams, about 20 grams to about 40 grams, about 20 grams to about 45 grams, about 20 grams to about 50 grams, about 20 grams to about 60 grams, about 25 grams to about 30 grams, about 25 grams to about 35 grams, about 25 grams to about 40 grams, about 25 grams to about 45 grams, about 25 grams to about 50 grams, about 25 grams to about 60 grams, about 30 grams to about 35 grams, about 30 grams to about 40 grams, about 30 grams to about 45 grams, about 30 grams to about 50 grams, about 30 grams to about 60 grams, about 35 grams to about 40 grams, about 35 grams to about 45 grams, about 35 grams to about 50 grams, about 35 grams to about 60 grams, about 40 grams to about 45 grams, about 40 grams to about 50 grams, about 40 grams to about 60 grams, about 45 grams to about 50 grams, about 45 grams to about 60 grams, or about 50 grams to about 60 grams. In some embodiments, the composition comprises a source of dietary protein in the amount of about 1 gram, about 5 grams, about 10 grams, about 15 grams, about 20 grams, about 25 grams, about 30 grams, about 35 grams, about 40 grams, about 45 grams, about 50 grams, or about 60 grams. In some embodiments, the composition comprises a source of dietary protein in the amount of at least about 1 gram, about 5 grams, about 10 grams, about 15 grams, about 20 grams, about 25 grams, about 30 grams, about 35 grams, about 40 grams, about 45 grams, or about 50 grams. In some embodiments, the composition comprises a source of dietary protein in the amount of at most about 5 grams, about 10 grams, about 15 grams, about 20 grams, about 25 grams, about 30 grams, about 35 grams, about 40 grams, about 45 grams, about 50 grams, or about 60 grams.

Dietary Fiber

In certain embodiments, the compositions disclosed herein may incorporate dietary fiber, which can comprise a group of plant-based carbohydrates that are not digested in the small intestine. Dietary fiber plays an essential role in maintaining gut health and function. Dietary fiber can also function to add bulk to the diet, aid in digestion, and can help prevent constipation by promoting regular bowel movements. Fiber can further be categorized into soluble fiber and insoluble fiber. Soluble fiber dissolves in water and forms a gel-like substance in the stomach, slowing down digestion and contributing to feelings of fullness, which can help with weight management. It can also lower levels of LDL (bad) cholesterol, regulate blood sugar levels, and support heart health. Insoluble fiber, on the other hand, does not dissolve in water and can aid digestive health by adding bulk to stools, helping to prevent constipation and promote regularity. Dietary fiber can also act as a prebiotic, providing nourishment for beneficial gut bacteria and promoting a healthy gut microbiota, which is linked to a wide range of health benefits, from mental health to immune function and weight management. In certain embodiments, fiber can appear in several forms, including but not limited to, psyllium husk, inulin, beta-glucans, cellulose, hemicellulose, pectin, and gums such as guar gum or xanthan gum. Given the potential health benefits and the fact that many individuals do not consume sufficient fiber through diet alone, supplementing with fiber can be beneficial. The incorporation of dietary fiber in the compositions disclosed herein can contribute to overall gut health, support weight management, and promote cardiovascular health, making it a valuable component for a wide range of individuals, including those with specific dietary needs and aging populations.

In some embodiments, the composition comprises one or more sources of dietary fiber in the amount of about 3 grams to about 50 grams. In some embodiments, the composition comprises one or more sources of dietary fiber in the amount of about 3 grams to about 4 grams, about 3 grams to about 5 grams, about 3 grams to about 10 grams, about 3 grams to about 20 grams, about 3 grams to about 21 grams, about 3 grams to about 25 grams, about 3 grams to about 30 grams, about 3 grams to about 35 grams, about 3 grams to about 38 grams, about 3 grams to about 40 grams, about 3 grams to about 50 grams, about 4 grams to about 5 grams, about 4 grams to about 10 grams, about 4 grams to about 20 grams, about 4 grams to about 21 grams, about 4 grams to about 25 grams, about 4 grams to about 30 grams, about 4 grams to about 35 grams, about 4 grams to about 38 grams, about 4 grams to about 40 grams, about 4 grams to about 50 grams, about 5 grams to about 10 grams, about 5 grams to about 20 grams, about 5 grams to about 21 grams, about 5 grams to about 25 grams, about 5 grams to about 30 grams, about 5 grams to about 35 grams, about 5 grams to about 38 grams, about 5 grams to about 40 grams, about 5 grams to about 50 grams, about 10 grams to about 20 grams, about 10 grams to about 21 grams, about 10 grams to about 25 grams, about 10 grams to about 30 grams, about 10 grams to about 35 grams, about 10 grams to about 38 grams, about 10 grams to about 40 grams, about 10 grams to about 50 grams, about 20 grams to about 21 grams, about 20 grams to about 25 grams, about 20 grams to about 30 grams, about 20 grams to about 35 grams, about 20 grams to about 38 grams, about 20 grams to about 40 grams, about 20 grams to about 50 grams, about 21 grams to about 25 grams, about 21 grams to about 30 grams, about 21 grams to about 35 grams, about 21 grams to about 38 grams, about 21 grams to about 40 grams, about 21 grams to about 50 grams, about 25 grams to about 30 grams, about 25 grams to about 35 grams, about 25 grams to about 38 grams, about 25 grams to about 40 grams, about 25 grams to about 50 grams, about 30 grams to about 35 grams, about 30 grams to about 38 grams, about 30 grams to about 40 grams, about 30 grams to about 50 grams, about 35 grams to about 38 grams, about 35 grams to about 40 grams, about 35 grams to about 50 grams, about 38 grams to about 40 grams, about 38 grams to about 50 grams, or about 40 grams to about 50 grams. In some embodiments, the composition comprises one or more sources of dietary fiber in the amount of about 3 grams, about 4 grams, about 5 grams, about 10 grams, about 20 grams, about 21 grams, about 25 grams, about 30 grams, about 35 grams, about 38 grams, about 40 grams, or about 50 grams. In some embodiments, the composition comprises one or more sources of dietary fiber in the amount of at least about 3 grams, about 4 grams, about 5 grams, about 10 grams, about 20 grams, about 21 grams, about 25 grams, about 30 grams, about 35 grams, about 38 grams, or about 40 grams. In some embodiments, the composition comprises one or more sources of dietary fiber in the amount of at most about 4 grams, about 5 grams, about 10 grams, about 20 grams, about 21 grams, about 25 grams, about 30 grams, about 35 grams, about 38 grams, about 40 grams, or about 50 grams.

Skin and Tissue Health

In another aspect, the compositions disclosed herein serve to maintain and/or promote the health of skin and various bodily tissues. In some embodiments, the compositions provided herein comprise one or more components that bolster the structural integrity, hydration, and cellular regeneration of tissues, which may contribute to the overall health and vitality of skin and other connective tissues. This can include, but is not limited to, the skin's elasticity, hydration levels, clarity, smoothness, and ability to regenerate and heal. A healthy skin state can also refer to the absence or reduced presence of harmful conditions or disorders, such as inflammation, infection, age spots, wrinkles, or diseases. In some instances, improved skin and tissue health outcomes can comprise resilience to damage, and healing processes, absence or reduced presence of harmful conditions or disorders, such as inflammation and infection. In some instances, uptake of various structural proteins and polysaccharides can contribute to improved health of skin and bodily tissues. Non-limiting examples of structural proteins and polysaccharides can include hyaluronic acid, chondroitin sulfate, biotin, glucosamine, beta-glucans, polymannuronic acid, collagen, keratin, elastin, fibrillin, and silk proteins.

Hyaluronic Acid

In another aspect, the compositions and formulations hereof may be employed to support skin, joint, and eye health, such as through the inclusion of hyaluronic acid. Hyaluronic acid, a naturally occurring polysaccharide in the body, in some instances, functions to hydrate the skin and maintain synovial fluid levels in joints. Due to its water-retaining properties, hyaluronic acid may confer the effect of maintaining skin elasticity and resilience. With age and exposure to various environmental factors, the body's natural hyaluronic acid levels may decrease, which can contribute to skin dryness, wrinkles, and joint discomfort. Hyaluronic acid supplementation may support skin and tissue health, which can include enhancing skin hydration, reducing the appearance of fine lines and wrinkles, promoting collagen synthesis, and supporting joint health.

In some embodiments, the composition comprises about 50 milligrams of hyaluronic acid to about 2,000 milligrams of hyaluronic acid. In some embodiments, the composition comprises about 50 milligrams of hyaluronic acid to about 100 milligrams of hyaluronic acid, about 50 milligrams of hyaluronic acid to about 150 milligrams of hyaluronic acid, about 50 milligrams of hyaluronic acid to about 200 milligrams of hyaluronic acid, about 50 milligrams of hyaluronic acid to about 250 milligrams of hyaluronic acid, about 50 milligrams of hyaluronic acid to about 300 milligrams of hyaluronic acid, about 50 milligrams of hyaluronic acid to about 350 milligrams of hyaluronic acid, about 50 milligrams of hyaluronic acid to about 400 milligrams of hyaluronic acid, about 50 milligrams of hyaluronic acid to about 450 milligrams of hyaluronic acid, about 50 milligrams of hyaluronic acid to about 500 milligrams of hyaluronic acid, about 50 milligrams of hyaluronic acid to about 1,000 milligrams of hyaluronic acid, about 50 milligrams of hyaluronic acid to about 2,000 milligrams of hyaluronic acid, about 100 milligrams of hyaluronic acid to about 150 milligrams of hyaluronic acid, about 100 milligrams of hyaluronic acid to about 200 milligrams of hyaluronic acid, about 100 milligrams of hyaluronic acid to about 250 milligrams of hyaluronic acid, about 100 milligrams of hyaluronic acid to about 300 milligrams of hyaluronic acid, about 100 milligrams of hyaluronic acid to about 350 milligrams of hyaluronic acid, about 100 milligrams of hyaluronic acid to about 400 milligrams of hyaluronic acid, about 100 milligrams of hyaluronic acid to about 450 milligrams of hyaluronic acid, about 100 milligrams of hyaluronic acid to about 500 milligrams of hyaluronic acid, about 100 milligrams of hyaluronic acid to about 1,000 milligrams of hyaluronic acid, about 100 milligrams of hyaluronic acid to about 2,000 milligrams of hyaluronic acid, about 150 milligrams of hyaluronic acid to about 200 milligrams of hyaluronic acid, about 150 milligrams of hyaluronic acid to about 250 milligrams of hyaluronic acid, about 150 milligrams of hyaluronic acid to about 300 milligrams of hyaluronic acid, about 150 milligrams of hyaluronic acid to about 350 milligrams of hyaluronic acid, about 150 milligrams of hyaluronic acid to about 400 milligrams of hyaluronic acid, about 150 milligrams of hyaluronic acid to about 450 milligrams of hyaluronic acid, about 150 milligrams of hyaluronic acid to about 500 milligrams of hyaluronic acid, about 150 milligrams of hyaluronic acid to about 1,000 milligrams of hyaluronic acid, about 150 milligrams of hyaluronic acid to about 2,000 milligrams of hyaluronic acid, about 200 milligrams of hyaluronic acid to about 250 milligrams of hyaluronic acid, about 200 milligrams of hyaluronic acid to about 300 milligrams of hyaluronic acid, about 200 milligrams of hyaluronic acid to about 350 milligrams of hyaluronic acid, about 200 milligrams of hyaluronic acid to about 400 milligrams of hyaluronic acid, about 200 milligrams of hyaluronic acid to about 450 milligrams of hyaluronic acid, about 200 milligrams of hyaluronic acid to about 500 milligrams of hyaluronic acid, about 200 milligrams of hyaluronic acid to about 1,000 milligrams of hyaluronic acid, about 200 milligrams of hyaluronic acid to about 2,000 milligrams of hyaluronic acid, about 250 milligrams of hyaluronic acid to about 300 milligrams of hyaluronic acid, about 250 milligrams of hyaluronic acid to about 350 milligrams of hyaluronic acid, about 250 milligrams of hyaluronic acid to about 400 milligrams of hyaluronic acid, about 250 milligrams of hyaluronic acid to about 450 milligrams of hyaluronic acid, about 250 milligrams of hyaluronic acid to about 500 milligrams of hyaluronic acid, about 250 milligrams of hyaluronic acid to about 1,000 milligrams of hyaluronic acid, about 250 milligrams of hyaluronic acid to about 2,000 milligrams of hyaluronic acid, about 300 milligrams of hyaluronic acid to about 350 milligrams of hyaluronic acid, about 300 milligrams of hyaluronic acid to about 400 milligrams of hyaluronic acid, about 300 milligrams of hyaluronic acid to about 450 milligrams of hyaluronic acid, about 300 milligrams of hyaluronic acid to about 500 milligrams of hyaluronic acid, about 300 milligrams of hyaluronic acid to about 1,000 milligrams of hyaluronic acid, about 300 milligrams of hyaluronic acid to about 2,000 milligrams of hyaluronic acid, about 350 milligrams of hyaluronic acid to about 400 milligrams of hyaluronic acid, about 350 milligrams of hyaluronic acid to about 450 milligrams of hyaluronic acid, about 350 milligrams of hyaluronic acid to about 500 milligrams of hyaluronic acid, about 350 milligrams of hyaluronic acid to about 1,000 milligrams of hyaluronic acid, about 350 milligrams of hyaluronic acid to about 2,000 milligrams of hyaluronic acid, about 400 milligrams of hyaluronic acid to about 450 milligrams of hyaluronic acid, about 400 milligrams of hyaluronic acid to about 500 milligrams of hyaluronic acid, about 400 milligrams of hyaluronic acid to about 1,000 milligrams of hyaluronic acid, about 400 milligrams of hyaluronic acid to about 2,000 milligrams of hyaluronic acid, about 450 milligrams of hyaluronic acid to about 500 milligrams of hyaluronic acid, about 450 milligrams of hyaluronic acid to about 1,000 milligrams of hyaluronic acid, about 450 milligrams of hyaluronic acid to about 2,000 milligrams of hyaluronic acid, about 500 milligrams of hyaluronic acid to about 1,000 milligrams of hyaluronic acid, about 500 milligrams of hyaluronic acid to about 2,000 milligrams of hyaluronic acid, or about 1,000 milligrams of hyaluronic acid to about 2,000 milligrams of hyaluronic acid. In some embodiments, the composition comprises about 50 milligrams of hyaluronic acid, about 100 milligrams of hyaluronic acid, about 150 milligrams of hyaluronic acid, about 200 milligrams of hyaluronic acid, about 250 milligrams of hyaluronic acid, about 300 milligrams of hyaluronic acid, about 350 milligrams of hyaluronic acid, about 400 milligrams of hyaluronic acid, about 450 milligrams of hyaluronic acid, about 500 milligrams of hyaluronic acid, about 1,000 milligrams of hyaluronic acid, or about 2,000 milligrams of hyaluronic acid. In some embodiments, the composition comprises at least about 50 milligrams of hyaluronic acid, about 100 milligrams of hyaluronic acid, about 150 milligrams of hyaluronic acid, about 200 milligrams of hyaluronic acid, about 250 milligrams of hyaluronic acid, about 300 milligrams of hyaluronic acid, about 350 milligrams of hyaluronic acid, about 400 milligrams of hyaluronic acid, about 450 milligrams of hyaluronic acid, about 500 milligrams of hyaluronic acid, or about 1,000 milligrams of hyaluronic acid. In some embodiments, the composition comprises at most about 100 milligrams of hyaluronic acid, about 150 milligrams of hyaluronic acid, about 200 milligrams of hyaluronic acid, about 250 milligrams of hyaluronic acid, about 300 milligrams of hyaluronic acid, about 350 milligrams of hyaluronic acid, about 400 milligrams of hyaluronic acid, about 450 milligrams of hyaluronic acid, about 500 milligrams of hyaluronic acid, about 1,000 milligrams of hyaluronic acid, or about 2,000 milligrams of hyaluronic acid.

Collagen

In several embodiments, the disclosed compositions include collagen, a key structural protein abundant in skin, hair, nails, and connective tissues including bones, tendons, and ligaments. Collagen plays a vital role in maintaining skin elasticity and strength, as well as promoting joint health. With aging, the body's natural collagen production declines, contributing to skin aging signs such as wrinkles and loss of elasticity, and potentially leading to joint discomfort due to the wear and tear of connective tissues. Supplementing with collagen has been shown to help counteract these effects. Studies have suggested that collagen supplementation may improve skin hydration and elasticity, reduce visible signs of aging, and support joint health. Additionally, some forms of collagen may be rich in specific amino acids that are essential for maintaining healthy hair and nails. In some instances, the compositions disclosed herein may comprise collagen in the form of collagen peptides and/or hydrolyzed collagen. Forms of collagen, as contemplated in the compositions described herein can include, but are not limited to, type I collagen, type II collagen, type III collagen, multi-collagen, and vegan collagen. Given the wide-ranging benefits of collagen, supplementation with collagen may be particularly beneficial for aging populations by functioning to, by way of non-limiting examples, support the maintenance of healthy skin, hair, nails, and joints, contribute to overall wellness, and promote a more youthful appearance.

In some embodiments, the composition comprises collagen from about 1 gram to about 25 grams. In some embodiments, the composition comprises collagen from about 1 gram to about 2.5 grams, about 1 gram to about 5 grams, about 1 gram to about 10 grams, about 1 gram to about 11 grams, about 1 gram to about 12 grams, about 1 gram to about 13 grams, about 1 gram to about 14 grams, about 1 gram to about 15 grams, about 1 gram to about 20 grams, about 1 gram to about 25 grams, about 2.5 grams to about 5 grams, about 2.5 grams to about 10 grams, about 2.5 grams to about 11 grams, about 2.5 grams to about 12 grams, about 2.5 grams to about 13 grams, about 2.5 grams to about 14 grams, about 2.5 grams to about 15 grams, about 2.5 grams to about 20 grams, about 2.5 grams to about 25 grams, about 5 grams to about 10 grams, about 5 grams to about 11 grams, about 5 grams to about 12 grams, about 5 grams to about 13 grams, about 5 grams to about 14 grams, about 5 grams to about 15 grams, about 5 grams to about 20 grams, about 5 grams to about 25 grams, about 10 grams to about 11 grams, about 10 grams to about 12 grams, about 10 grams to about 13 grams, about 10 grams to about 14 grams, about 10 grams to about 15 grams, about 10 grams to about 20 grams, about 10 grams to about 25 grams, about 11 grams to about 12 grams, about 11 grams to about 13 grams, about 11 grams to about 14 grams, about 11 grams to about 15 grams, about 11 grams to about 20 grams, about 11 grams to about 25 grams, about 12 grams to about 13 grams, about 12 grams to about 14 grams, about 12 grams to about 15 grams, about 12 grams to about 20 grams, about 12 grams to about 25 grams, about 13 grams to about 14 grams, about 13 grams to about 15 grams, about 13 grams to about 20 grams, about 13 grams to about 25 grams, about 14 grams to about 15 grams, about 14 grams to about 20 grams, about 14 grams to about 25 grams, about 15 grams to about 20 grams, about 15 grams to about 25 grams, or about 20 grams to about 25 grams. In some embodiments, the composition comprises collagen from about 1 gram, about 2.5 grams, about 5 grams, about 10 grams, about 11 grams, about 12 grams, about 13 grams, about 14 grams, about 15 grams, about 20 grams, or about 25 grams. In some embodiments, the composition comprises collagen from at least about 1 gram, about 2.5 grams, about 5 grams, about 10 grams, about 11 grams, about 12 grams, about 13 grams, about 14 grams, about 15 grams, or about 20 grams. In some embodiments, the composition comprises collagen from at most about 2.5 grams, about 5 grams, about 10 grams, about 11 grams, about 12 grams, about 13 grams, about 14 grams, about 15 grams, about 20 grams, or about 25 grams.

Biotin

In some embodiments, the compositions presented herein incorporate biotin, also known as vitamin B7 or vitamin H. Biotin is a water-soluble vitamin that acts as an essential coenzyme in the metabolism of proteins, fats, and carbohydrates, which may contribute to energy production within cells. In some aspects, biotin acts as a co-factor for carboxylases, which can serve key functions in gluconeogenesis, fatty acid synthesis, and the metabolism of certain amino acids. Deficiencies in biotin may lead to symptoms such as skin rashes, hair loss, and brittle nails. In additional aspects, biotin can function to support nervous system function (e.g., maintenance of myeline sheath integrity, neuron signaling functionality, and neurotransmitter activity, etc.) and, in some aspects, required for the function of certain enzymes in the body (e.g., biotin-dependent enzymes involved in embryonic cell growth, production of fatty acids, and metabolism of glucose and amino acids, etc). Aging populations may particularly benefit from biotin supplementation. Supplementation with biotin may support metabolic function, skin health, and the maintenance of hair, which can be areas of concern with age.

In some embodiments, the composition comprises biotin in the amount of about 5 micrograms to about 25,000 micrograms. In some embodiments, the composition comprises biotin in the amount of about 5 micrograms to about 10 micrograms, about 5 micrograms to about 20 micrograms, about 5 micrograms to about 30 micrograms, about 5 micrograms to about 40 micrograms, about 5 micrograms to about 50 micrograms, about 5 micrograms to about 100 micrograms, about 5 micrograms to about 500 micrograms, about 5 micrograms to about 1,000 micrograms, about 5 micrograms to about 5,000 micrograms, about 5 micrograms to about 10,000 micrograms, about 5 micrograms to about 25,000 micrograms, about 10 micrograms to about 20 micrograms, about 10 micrograms to about 30 micrograms, about 10 micrograms to about 40 micrograms, about 10 micrograms to about 50 micrograms, about 10 micrograms to about 100 micrograms, about 10 micrograms to about 500 micrograms, about 10 micrograms to about 1,000 micrograms, about 10 micrograms to about 5,000 micrograms, about 10 micrograms to about 10,000 micrograms, about 10 micrograms to about 25,000 micrograms, about 20 micrograms to about 30 micrograms, about 20 micrograms to about 40 micrograms, about 20 micrograms to about 50 micrograms, about 20 micrograms to about 100 micrograms, about 20 micrograms to about 500 micrograms, about 20 micrograms to about 1,000 micrograms, about 20 micrograms to about 5,000 micrograms, about 20 micrograms to about 10,000 micrograms, about 20 micrograms to about 25,000 micrograms, about 30 micrograms to about 40 micrograms, about 30 micrograms to about 50 micrograms, about 30 micrograms to about 100 micrograms, about 30 micrograms to about 500 micrograms, about 30 micrograms to about 1,000 micrograms, about 30 micrograms to about 5,000 micrograms, about 30 micrograms to about 10,000 micrograms, about 30 micrograms to about 25,000 micrograms, about 40 micrograms to about 50 micrograms, about 40 micrograms to about 100 micrograms, about 40 micrograms to about 500 micrograms, about 40 micrograms to about 1,000 micrograms, about 40 micrograms to about 5,000 micrograms, about 40 micrograms to about 10,000 micrograms, about 40 micrograms to about 25,000 micrograms, about 50 micrograms to about 100 micrograms, about 50 micrograms to about 500 micrograms, about 50 micrograms to about 1,000 micrograms, about 50 micrograms to about 5,000 micrograms, about 50 micrograms to about 10,000 micrograms, about 50 micrograms to about 25,000 micrograms, about 100 micrograms to about 500 micrograms, about 100 micrograms to about 1,000 micrograms, about 100 micrograms to about 5,000 micrograms, about 100 micrograms to about 10,000 micrograms, about 100 micrograms to about 25,000 micrograms, about 500 micrograms to about 1,000 micrograms, about 500 micrograms to about 5,000 micrograms, about 500 micrograms to about 10,000 micrograms, about 500 micrograms to about 25,000 micrograms, about 1,000 micrograms to about 5,000 micrograms, about 1,000 micrograms to about 10,000 micrograms, about 1,000 micrograms to about 25,000 micrograms, about 5,000 micrograms to about 10,000 micrograms, about 5,000 micrograms to about 25,000 micrograms, or about 10,000 micrograms to about 25,000 micrograms. In some embodiments, the composition comprises biotin in the amount of about 5 micrograms, about 10 micrograms, about 20 micrograms, about 30 micrograms, about 40 micrograms, about 50 micrograms, about 100 micrograms, about 500 micrograms, about 1,000 micrograms, about 5,000 micrograms, about 10,000 micrograms, or about 25,000 micrograms. In some embodiments, the composition comprises biotin in the amount of at least about 5 micrograms, about 10 micrograms, about 20 micrograms, about 30 micrograms, about 40 micrograms, about 50 micrograms, about 100 micrograms, about 500 micrograms, about 1,000 micrograms, about 5,000 micrograms, or about 10,000 micrograms. In some embodiments, the composition comprises biotin in the amount of at most about 10 micrograms, about 20 micrograms, about 30 micrograms, about 40 micrograms, about 50 micrograms, about 100 micrograms, about 500 micrograms, about 1,000 micrograms, about 5,000 micrograms, about 10,000 micrograms, or about 25,000 micrograms.

Antioxidants and Cardiovascular Health

In one of many aspects, the compositions provided herein comprise one or more components that function as antioxidants. Non-limiting examples of molecules with the capacity for antioxidant function may include vitamin C, vitamin E, vitamin A, beta-carotene, lycopene, lutein, selenium, manganese, zeaxanthin, flavonoids, polyphenols, phytoestrogens, anthocyanins, coenzyme Q10 (CoQ10), glutathione, melatonin, catechins, resveratrol, ellagic acid, and quercetin. In some instances, oxidative stress, characterized by an imbalance between free radicals and antioxidants in the body, may be a significant contributor to cardiovascular diseases. Antioxidants are molecules that can neutralize these free radicals, reducing oxidative stress, which may confer the effect of preventing or slowing the progression of cardiovascular diseases or conditions. Supplementation with antioxidants may also function to improve blood lipid profiles, promote vascular health, maintain heart function, protect against oxidative damage, and contribute towards longevity and cardiovascular wellbeing.

Coenzyme Q10

Coenzyme Q10, also known as ubiquinone, CoQ10, or CoQ, is a fat-soluble compound found in all cells. CoQ10, in some aspects, plays a critical role in redox reactions in mitochondria, functioning as an electron carrier during oxidative phosphorylation, and aiding the conversion of nutrients into ATP. CoQ10 also possesses antioxidant properties. CoQ10 levels in the human body can decrease with age and certain health conditions, making supplementation potentially beneficial. CoQ10 supplementation may support heart health, aid in energy production, and enhance antioxidant protection. As contemplated in the compositions disclosed herein, CoQ10 may be available as ubiquinol, the active antioxidant form, and ubiquinone, the oxidized form, which the body partially converts to ubiquinol. Increased production of reactive oxygen species (ROS), which can occur during exhaustive exercise, may result in the depletion of CoQ10 levels in muscle tissue and may adversely impact exercise performance. Supplementing with CoQ10 may increase the concentration of this compound in muscle tissue, enhancing free radical scavenging activity and may contribute to improved exercise performance (e.g., during repeated bouts of high-intensity, short-duration exercise).

In some embodiments, the composition comprises about 50 milligrams of CoQ10 to about 2,000 milligrams of CoQ10. In some embodiments, the composition comprises about 50 milligrams of CoQ10 to about 75 milligrams of CoQ10, about 50 milligrams of CoQ10 to about 100 milligrams of CoQ10, about 50 milligrams of CoQ10 to about 125 milligrams of CoQ10, about 50 milligrams of CoQ10 to about 150 milligrams of CoQ10, about 50 milligrams of CoQ10 to about 175 milligrams of CoQ10, about 50 milligrams of CoQ10 to about 200 milligrams of CoQ10, about 50 milligrams of CoQ10 to about 225 milligrams of CoQ10, about 50 milligrams of CoQ10 to about 250 milligrams of CoQ10, about 50 milligrams of CoQ10 to about 500 milligrams of CoQ10, about 50 milligrams of CoQ10 to about 1,000 milligrams of CoQ10, about 50 milligrams of CoQ10 to about 2,000 milligrams of CoQ10, about 75 milligrams of CoQ10 to about 100 milligrams of CoQ10, about 75 milligrams of CoQ10 to about 125 milligrams of CoQ10, about 75 milligrams of CoQ10 to about 150 milligrams of CoQ10, about 75 milligrams of CoQ10 to about 175 milligrams of CoQ10, about 75 milligrams of CoQ10 to about 200 milligrams of CoQ10, about 75 milligrams of CoQ10 to about 225 milligrams of CoQ10, about 75 milligrams of CoQ10 to about 250 milligrams of CoQ10, about 75 milligrams of CoQ10 to about 500 milligrams of CoQ10, about 75 milligrams of CoQ10 to about 1,000 milligrams of CoQ10, about 75 milligrams of CoQ10 to about 2,000 milligrams of CoQ10, about 100 milligrams of CoQ10 to about 125 milligrams of CoQ10, about 100 milligrams of CoQ10 to about 150 milligrams of CoQ10, about 100 milligrams of CoQ10 to about 175 milligrams of CoQ10, about 100 milligrams of CoQ10 to about 200 milligrams of CoQ10, about 100 milligrams of CoQ10 to about 225 milligrams of CoQ10, about 100 milligrams of CoQ10 to about 250 milligrams of CoQ10, about 100 milligrams of CoQ10 to about 500 milligrams of CoQ10, about 100 milligrams of CoQ10 to about 1,000 milligrams of CoQ10, about 100 milligrams of CoQ10 to about 2,000 milligrams of CoQ10, about 125 milligrams of CoQ10 to about 150 milligrams of CoQ10, about 125 milligrams of CoQ10 to about 175 milligrams of CoQ10, about 125 milligrams of CoQ10 to about 200 milligrams of CoQ10, about 125 milligrams of CoQ10 to about 225 milligrams of CoQ10, about 125 milligrams of CoQ10 to about 250 milligrams of CoQ10, about 125 milligrams of CoQ10 to about 500 milligrams of CoQ10, about 125 milligrams of CoQ10 to about 1,000 milligrams of CoQ10, about 125 milligrams of CoQ10 to about 2,000 milligrams of CoQ10, about 150 milligrams of CoQ10 to about 175 milligrams of CoQ10, about 150 milligrams of CoQ10 to about 200 milligrams of CoQ10, about 150 milligrams of CoQ10 to about 225 milligrams of CoQ10, about 150 milligrams of CoQ10 to about 250 milligrams of CoQ10, about 150 milligrams of CoQ10 to about 500 milligrams of CoQ10, about 150 milligrams of CoQ10 to about 1,000 milligrams of CoQ10, about 150 milligrams of CoQ10 to about 2,000 milligrams of CoQ10, about 175 milligrams of CoQ10 to about 200 milligrams of CoQ10, about 175 milligrams of CoQ10 to about 225 milligrams of CoQ10, about 175 milligrams of CoQ10 to about 250 milligrams of CoQ10, about 175 milligrams of CoQ10 to about 500 milligrams of CoQ10, about 175 milligrams of CoQ10 to about 1,000 milligrams of CoQ10, about 175 milligrams of CoQ10 to about 2,000 milligrams of CoQ10, about 200 milligrams of CoQ10 to about 225 milligrams of CoQ10, about 200 milligrams of CoQ10 to about 250 milligrams of CoQ10, about 200 milligrams of CoQ10 to about 500 milligrams of CoQ10, about 200 milligrams of CoQ10 to about 1,000 milligrams of CoQ10, about 200 milligrams of CoQ10 to about 2,000 milligrams of CoQ10, about 225 milligrams of CoQ10 to about 250 milligrams of CoQ10, about 225 milligrams of CoQ10 to about 500 milligrams of CoQ10, about 225 milligrams of CoQ10 to about 1,000 milligrams of CoQ10, about 225 milligrams of CoQ10 to about 2,000 milligrams of CoQ10, about 250 milligrams of CoQ10 to about 500 milligrams of CoQ10, about 250 milligrams of CoQ10 to about 1,000 milligrams of CoQ10, about 250 milligrams of CoQ10 to about 2,000 milligrams of CoQ10, about 500 milligrams of CoQ10 to about 1,000 milligrams of CoQ10, about 500 milligrams of CoQ10 to about 2,000 milligrams of CoQ10, or about 1,000 milligrams of CoQ10 to about 2,000 milligrams of CoQ10. In some embodiments, the composition comprises about 50 milligrams of CoQ10, about 75 milligrams of CoQ10, about 100 milligrams of CoQ10, about 125 milligrams of CoQ10, about 150 milligrams of CoQ10, about 175 milligrams of CoQ10, about 200 milligrams of CoQ10, about 225 milligrams of CoQ10, about 250 milligrams of CoQ10, about 500 milligrams of CoQ10, about 1,000 milligrams of CoQ10, or about 2,000 milligrams of CoQ10. In some embodiments, the composition comprises at least about 50 milligrams of CoQ10, about 75 milligrams of CoQ10, about 100 milligrams of CoQ10, about 125 milligrams of CoQ10, about 150 milligrams of CoQ10, about 175 milligrams of CoQ10, about 200 milligrams of CoQ10, about 225 milligrams of CoQ10, about 250 milligrams of CoQ10, about 500 milligrams of CoQ10, or about 1,000 milligrams of CoQ10. In some embodiments, the composition comprises at most about 75 milligrams of CoQ10, about 100 milligrams of CoQ10, about 125 milligrams of CoQ10, about 150 milligrams of CoQ10, about 175 milligrams of CoQ10, about 200 milligrams of CoQ10, about 225 milligrams of CoQ10, about 250 milligrams of CoQ10, about 500 milligrams of CoQ10, about 1,000 milligrams of CoQ10, or about 2,000 milligrams of CoQ10.

Trans-Resveratrol

Various embodiments of the compositions disclosed herein may incorporate trans-resveratrol, a naturally occurring polyphenol which can be found in several plants, including, but not limited to, the skin of grapes, blueberries, raspberries, and mulberries. As a dietary supplement, trans-resveratrol has been recognized for its potential health benefits. Functioning as an antioxidant, trans-resveratrol can help protect the body's cells from damage by free radicals, unstable molecules that can contribute to chronic diseases and aging, thus supporting overall cellular health. Additionally, trans-resveratrol has been associated with potential anti-inflammatory effects. By aiding in the reduction of inflammation, it can support the body's overall health and well-being, particularly as chronic inflammation can be linked to many serious diseases such as heart disease, cancer, diabetes, and Alzheimer's disease. Trans-resveratrol has also been studied for its heart health benefits, which include, but are not limited to, improving heart function, reducing LDL cholesterol levels, and enhancing the body's antioxidant defenses, potentially helping prevent the oxidation of LDL cholesterol, a key step in the development of atherosclerosis. Furthermore, in additional aspects, trans-resveratrol may support healthy aging and longevity, and may offer benefits for brain health and cognitive function, as well as support healthy metabolic function. Supplementation with trans-resveratrol may confer a range of potential health benefits, including, but not limited to, antioxidant and anti-inflammatory effects, cardiovascular support, and anti-aging benefits.

In some embodiments, the composition comprises trans-resveratrol in the amount of about 100 milligrams to about 2,000 milligrams. In some embodiments, the composition comprises trans-resveratrol in the amount of about 100 milligrams to about 150 milligrams, about 100 milligrams to about 200 milligrams, about 100 milligrams to about 250 milligrams, about 100 milligrams to about 300 milligrams, about 100 milligrams to about 350 milligrams, about 100 milligrams to about 400 milligrams, about 100 milligrams to about 450 milligrams, about 100 milligrams to about 500 milligrams, about 100 milligrams to about 1,000 milligrams, about 100 milligrams to about 1,500 milligrams, about 100 milligrams to about 2,000 milligrams, about 150 milligrams to about 200 milligrams, about 150 milligrams to about 250 milligrams, about 150 milligrams to about 300 milligrams, about 150 milligrams to about 350 milligrams, about 150 milligrams to about 400 milligrams, about 150 milligrams to about 450 milligrams, about 150 milligrams to about 500 milligrams, about 150 milligrams to about 1,000 milligrams, about 150 milligrams to about 1,500 milligrams, about 150 milligrams to about 2,000 milligrams, about 200 milligrams to about 250 milligrams, about 200 milligrams to about 300 milligrams, about 200 milligrams to about 350 milligrams, about 200 milligrams to about 400 milligrams, about 200 milligrams to about 450 milligrams, about 200 milligrams to about 500 milligrams, about 200 milligrams to about 1,000 milligrams, about 200 milligrams to about 1,500 milligrams, about 200 milligrams to about 2,000 milligrams, about 250 milligrams to about 300 milligrams, about 250 milligrams to about 350 milligrams, about 250 milligrams to about 400 milligrams, about 250 milligrams to about 450 milligrams, about 250 milligrams to about 500 milligrams, about 250 milligrams to about 1,000 milligrams, about 250 milligrams to about 1,500 milligrams, about 250 milligrams to about 2,000 milligrams, about 300 milligrams to about 350 milligrams, about 300 milligrams to about 400 milligrams, about 300 milligrams to about 450 milligrams, about 300 milligrams to about 500 milligrams, about 300 milligrams to about 1,000 milligrams, about 300 milligrams to about 1,500 milligrams, about 300 milligrams to about 2,000 milligrams, about 350 milligrams to about 400 milligrams, about 350 milligrams to about 450 milligrams, about 350 milligrams to about 500 milligrams, about 350 milligrams to about 1,000 milligrams, about 350 milligrams to about 1,500 milligrams, about 350 milligrams to about 2,000 milligrams, about 400 milligrams to about 450 milligrams, about 400 milligrams to about 500 milligrams, about 400 milligrams to about 1,000 milligrams, about 400 milligrams to about 1,500 milligrams, about 400 milligrams to about 2,000 milligrams, about 450 milligrams to about 500 milligrams, about 450 milligrams to about 1,000 milligrams, about 450 milligrams to about 1,500 milligrams, about 450 milligrams to about 2,000 milligrams, about 500 milligrams to about 1,000 milligrams, about 500 milligrams to about 1,500 milligrams, about 500 milligrams to about 2,000 milligrams, about 1,000 milligrams to about 1,500 milligrams, about 1,000 milligrams to about 2,000 milligrams, or about 1,500 milligrams to about 2,000 milligrams. In some embodiments, the composition comprises trans-resveratrol in the amount of about 100 milligrams, about 150 milligrams, about 200 milligrams, about 250 milligrams, about 300 milligrams, about 350 milligrams, about 400 milligrams, about 450 milligrams, about 500 milligrams, about 1,000 milligrams, about 1,500 milligrams, or about 2,000 milligrams. In some embodiments, the composition comprises trans-resveratrol in the amount of at least about 100 milligrams, about 150 milligrams, about 200 milligrams, about 250 milligrams, about 300 milligrams, about 350 milligrams, about 400 milligrams, about 450 milligrams, about 500 milligrams, about 1,000 milligrams, or about 1,500 milligrams. In some embodiments, the composition comprises trans-resveratrol in the amount of at most about 150 milligrams, about 200 milligrams, about 250 milligrams, about 300 milligrams, about 350 milligrams, about 400 milligrams, about 450 milligrams, about 500 milligrams, about 1,000 milligrams, about 1,500 milligrams, or about 2,000 milligrams.

Vitamins and Minerals

In various embodiments, the compositions disclosed herein may comprise one or more vitamins, vitamin complexes, minerals, and/or precursors or derivatives thereof. Vitamins are organic compounds that are required in small quantities by the body for normal growth, metabolism, and overall well-being. Different vitamins serve diverse functions: some contribute to energy production, others are crucial for tissue and cell repair, blood cell synthesis, or immune system function. Vitamin complexes may encompass combination products that incorporate multiple vitamins, often paired with minerals and other essential nutrients, into a single formulation. Minerals, inorganic substances that the body cannot synthesize, also perform a variety of biological functions, ranging from maintaining bone health and muscle function to supporting neural communication and enzyme activity. The presence of both vitamins and minerals in the disclosed compositions may contribute to a comprehensive nutrient profile, addressing multiple aspects of health in a single product. Given that the body's requirements for certain vitamins and minerals may increase with age, or due to certain lifestyle factors, certain compositions comprising one or more vitamins, vitamin complexes, minerals, and/or precursors or derivatives thereof can be particularly beneficial for ensuring adequate nutrient intake and promoting overall health, especially for aging populations and those with specific dietary needs.

Folate

The compositions disclosed herein can incorporate folate, or vitamin B9, an essential nutrient critical to numerous bodily functions. These include, but are not limited to, DNA synthesis and repair, cell division, and the production of red and white blood cells. Folate, especially in the form of folic acid or other derivatives, is vital for neural tube formation during early development, underscoring its importance for pregnant individuals as its deficiency can lead to neural tube defects. Folate is naturally found in a variety of foods such as leafy green vegetables, fruits, nuts, beans, and seafood. However, the naturally occurring folate can be reduced due to cooking and processing, potentially necessitating supplementation. With respect to folate supplementation, one may consider the distinction between bioavailability in naturally occurring folate relative to folic acid, its synthetic counterpart. Folic acid has higher bioavailability than naturally occurring folates, especially when taken on an empty stomach. This differential is accounted for using "micrograms of Dietary Folate Equivalents" (mcg DFE). For folic acid consumed with food or in fortified foods, 1 mcg is equivalent to 1.7 mcg DFE. However, if the folic acid supplement is consumed on an empty stomach, 1 mcg is equivalent to 2 mcg DFE. Maintaining adequate folate levels can be particularly significant in the aging population, for factors including, but not limited to, cognitive function and cardiovascular health. Folate, in conjunction with various B-vitamins, can contribute key functionality in regulating homocysteine levels—elevated levels of which can be associated with increased risks of cardiovascular disease and cognitive impairment. Therefore, the inclusion of folate in its natural form, or as folic acid or other derivatives, in the compositions contemplated herein can offer multiple potential health benefits including, but not limited to, supporting cellular health and cognitive function to promoting cardiovascular wellbeing, making it especially beneficial for aging populations and those adhering to specific dietary patterns.

In some embodiments, the composition comprises folate or a derivative thereof in the amount of about 5 micrograms to about 10,000 micrograms. In some embodiments, the composition comprises folate or a derivative thereof in the amount of about 5 micrograms to about 8.5 micrograms, about 5 micrograms to about 10 micrograms, about 5 micrograms to about 100 micrograms, about 5 micrograms to about 200 micrograms, about 5 micrograms to about 300 micrograms, about 5 micrograms to about 400 micrograms, about 5 micrograms to about 500 micrograms, about 5 micrograms to about 1,000 micrograms, about 5 micrograms to about 5,000 micrograms, about 5 micrograms to about 8,500 micrograms, about 5 micrograms to about 10,000 micrograms, about 8.5 micrograms to about 10 micrograms, about 8.5 micrograms to about 100 micrograms, about 8.5 micrograms to about 200 micrograms, about 8.5 micrograms to about 300 micrograms, about 8.5 micrograms to about 400 micrograms, about 8.5 micrograms to about 500 micrograms, about 8.5 micrograms to about 1,000 micrograms, about 8.5 micrograms to about 5,000 micrograms, about 8.5 micrograms to about 8,500 micrograms, about 8.5 micrograms to about 10,000 micrograms, about 10 micrograms to about 100 micrograms, about 10 micrograms to about 200 micrograms, about 10 micrograms to about 300 micrograms, about 10 micrograms to about 400 micrograms, about 10 micrograms to about 500 micrograms, about 10 micrograms to about 1,000 micrograms, about 10 micrograms to about 5,000 micrograms, about 10 micrograms to about 8,500 micrograms, about 10 micrograms to about 10,000 micrograms, about 100 micrograms to about 200 micrograms, about 100 micrograms to about 300 micrograms, about 100 micrograms to about 400 micrograms, about 100 micrograms to about 500 micrograms, about 100 micrograms to about 1,000 micrograms, about 100 micrograms to about 5,000 micrograms, about 100 micrograms to about 8,500 micrograms, about 100 micrograms to about 10,000 micrograms, about 200 micrograms to about 300 micrograms, about 200 micrograms to about 400 micrograms, about 200 micrograms to about 500 micrograms, about 200 micrograms to about 1,000 micrograms, about 200 micrograms to about 5,000 micrograms, about 200 micrograms to about 8,500 micrograms, about 200 micrograms to about 10,000 micrograms, about 300 micrograms to about 400 micrograms, about 300 micrograms to about 500 micrograms, about 300 micrograms to about 1,000 micrograms, about 300 micrograms to about 5,000 micrograms, about 300 micrograms to about 8,500 micrograms, about 300 micrograms to about 10,000 micrograms, about 400 micrograms to about 500 micrograms, about 400 micrograms to about 1,000 micrograms, about 400 micrograms to about 5,000 micrograms, about 400 micrograms to about 8,500 micrograms, about 400 micrograms to about 10,000 micrograms, about 500 micrograms to about 1,000 micrograms, about 500 micrograms to about 5,000 micrograms, about 500 micrograms to about 8,500 micrograms, about 500 micrograms to about 10,000 micrograms, about 1,000 micrograms to about 5,000 micrograms, about 1,000 micrograms to about 8,500 micrograms, about 1,000 micrograms to about 10,000 micrograms, about 5,000 micrograms to about 8,500 micrograms, about 5,000 micrograms to about 10,000 micrograms, or about 8,500 micrograms to about 10,000 micrograms. In some embodiments, the composition comprises folate or a derivative thereof in the amount of about 5 micrograms, about 8.5 micrograms, about 10 micrograms, about 100 micrograms, about 200 micrograms, about 300 micrograms, about 400 micrograms, about 500 micrograms, about 1,000 micrograms, about 5,000 micrograms, about 8,500 micrograms, or about 10,000 micrograms. In some embodiments, the composition comprises folate or a derivative thereof in the amount of at least about 5 micrograms, about 8.5 micrograms, about 10 micrograms, about 100 micrograms, about 200 micrograms, about 300 micrograms, about 400 micrograms, about 500 micrograms, about 1,000 micrograms, about 5,000 micrograms, or about 8,500 micrograms. In some embodiments, the composition comprises folate or a derivative thereof in the amount of at most about 8.5 micrograms, about 10 micrograms, about 100 micrograms, about 200 micrograms, about 300 micrograms, about 400 micrograms, about 500 micrograms, about 1,000 micrograms, about 5,000 micrograms, about 8,500 micrograms, or about 10,000 micrograms.

In some embodiments, the composition comprises folic acid in the amount of about 5 micrograms to about 10,000 micrograms. In some embodiments, the composition comprises folic acid in the amount of about 5 micrograms to about 8.5 micrograms, about 5 micrograms to about 10 micrograms, about 5 micrograms to about 100 micrograms, about 5 micrograms to about 200 micrograms, about 5 micrograms to about 300 micrograms, about 5 micrograms to about 400 micrograms, about 5 micrograms to about 500 micrograms, about 5 micrograms to about 1,000 micrograms, about 5 micrograms to about 5,000 micrograms, about 5 micrograms to about 8,500 micrograms, about 5 micrograms to about 10,000 micrograms, about 8.5 micrograms to about 10 micrograms, about 8.5 micrograms to about 100 micrograms, about 8.5 micrograms to about 200 micrograms, about 8.5 micrograms to about 300 micrograms, about 8.5 micrograms to about 400 micrograms, about 8.5 micrograms to about 500 micrograms, about 8.5 micrograms to about 1,000 micrograms, about 8.5 micrograms to about 5,000 micrograms, about 8.5 micrograms to about 8,500 micrograms, about 8.5 micrograms to about 10,000 micrograms, about 10 micrograms to about 100 micrograms, about 10 micrograms to about 200 micrograms, about 10 micrograms to about 300 micrograms, about 10 micrograms to about 400 micrograms, about 10 micrograms to about 500 micrograms, about 10 micrograms to about 1,000 micrograms, about 10 micrograms to about 5,000 micrograms, about 10 micrograms to about 8,500 micrograms, about 10 micrograms to about 10,000 micrograms, about 100 micrograms to about 200 micrograms, about 100 micrograms to about 300 micrograms, about 100 micrograms to about 400 micrograms, about 100 micrograms to about 500 micrograms, about 100 micrograms to about 1,000 micrograms, about 100 micrograms to about 5,000 micrograms, about 100 micrograms to about 8,500 micrograms, about 100 micrograms to about 10,000 micrograms, about 200 micrograms to about 300 micrograms, about 200 micrograms to about 400 micrograms, about 200 micrograms to about 500 micrograms, about 200 micrograms to about 1,000 micrograms, about 200 micrograms to about 5,000 micrograms, about 200 micrograms to about 8,500 micrograms, about 200 micrograms to about 10,000 micrograms, about 300 micrograms to about 400 micrograms, about 300 micrograms to about 500 micrograms, about 300 micrograms to about 1,000 micrograms, about 300 micrograms to about 5,000 micrograms, about 300 micrograms to about 8,500 micrograms, about 300 micrograms to about 10,000 micrograms, about 400 micrograms to about 500 micrograms, about 400 micrograms to about 1,000 micrograms, about 400 micrograms to about 5,000 micrograms, about 400 micrograms to about 8,500 micrograms, about 400 micrograms to about 10,000 micrograms, about 500 micrograms to about 1,000 micrograms, about 500 micrograms to about 5,000 micrograms, about 500 micrograms to about 8,500 micrograms, about 500 micrograms to about 10,000 micrograms, about 1,000 micrograms to about 5,000 micrograms, about 1,000 micrograms to about 8,500 micrograms, about 1,000 micrograms to about 10,000 micrograms, about 5,000 micrograms to about 8,500 micrograms, about 5,000 micrograms to about 10,000 micrograms, or about 8,500 micrograms to about 10,000 micrograms. In some embodiments, the composition comprises folic acid in the amount of about 5 micrograms, about 8.5 micrograms, about 10 micrograms, about 100 micrograms, about 200 micrograms, about 300 micrograms, about 400 micrograms, about 500 micrograms, about 1,000 micrograms, about 5,000 micrograms, about 8,500 micrograms, or about 10,000 micrograms. In some embodiments, the composition comprises folic acid in the amount of at least about 5 micrograms, about 8.5 micrograms, about 10 micrograms, about 100 micrograms, about 200 micrograms, about 300 micrograms, about 400 micrograms, about 500 micrograms, about 1,000 micrograms, about 5,000 micrograms, or about 8,500 micrograms. In some embodiments, the composition comprises folic acid in the amount of at most about 8.5 micrograms, about 10 micrograms, about 100 micrograms, about 200 micrograms, about 300 micrograms, about 400 micrograms, about 500 micrograms, about 1,000 micrograms, about 5,000 micrograms, about 8,500 micrograms, or about 10,000 micrograms.

In some embodiments, the composition comprises folic acid in the amount of about 5 micrograms DFE to about 10,000 micrograms DFE. In some embodiments, the composition comprises folic acid in the amount of about 5 micrograms DFE to about 8.5 micrograms DFE, about 5 micrograms DFE to about 10 micrograms DFE, about 5 micrograms DFE to about 100 micrograms DFE, about 5 micrograms DFE to about 200 micrograms DFE, about 5 micrograms DFE to about 300 micrograms DFE, about 5 micrograms DFE to about 400 micrograms DFE, about 5 micrograms DFE to about 500 micrograms DFE, about 5 micrograms DFE to about 1,000 micrograms DFE, about 5 micrograms DFE to about 5,000 micrograms DFE, about 5 micrograms DFE to about 8,500 micrograms DFE, about 5 micrograms DFE to about 10,000 micrograms DFE, about 8.5 micrograms DFE to about 10 micrograms DFE, about 8.5 micrograms DFE to about 100 micrograms DFE, about 8.5 micrograms DFE to about 200 micrograms DFE, about 8.5 micrograms DFE to about 300 micrograms DFE, about 8.5 micrograms DFE to about 400 micrograms DFE, about 8.5 micrograms DFE to about 500 micrograms DFE, about 8.5 micrograms DFE to about 1,000 micrograms DFE, about 8.5 micrograms DFE to about 5,000 micrograms DFE, about 8.5 micrograms DFE to about 8,500 micrograms DFE, about 8.5 micrograms DFE to about 10,000 micrograms DFE, about 10 micrograms DFE to about 100 micrograms DFE, about 10 micrograms DFE to about 200 micrograms DFE, about 10 micrograms DFE to about 300 micrograms DFE, about 10 micrograms DFE to about 400 micrograms DFE, about 10 micrograms DFE to about 500 micrograms DFE, about 10 micrograms DFE to about 1,000 micrograms DFE, about 10 micrograms DFE to about 5,000 micrograms DFE, about 10 micrograms DFE to about 8,500 micrograms DFE, about 10 micrograms DFE to about 10,000 micrograms DFE, about 100 micrograms DFE to about 200 micrograms DFE, about 100 micrograms DFE to about 300 micrograms DFE, about 100 micrograms DFE to about 400 micrograms DFE, about 100 micrograms DFE to about 500 micrograms DFE, about 100 micrograms DFE to about 1,000 micrograms DFE, about 100 micrograms DFE to about 5,000 micrograms DFE, about 100 micrograms DFE to about 8,500 micrograms DFE, about 100 micrograms DFE to about 10,000 micrograms DFE, about 200 micrograms DFE to about 300 micrograms DFE, about 200 micrograms DFE to about 400 micrograms DFE, about 200 micrograms DFE to about 500 micrograms DFE, about 200 micrograms DFE to about 1,000 micrograms DFE, about 200 micrograms DFE to about 5,000 micrograms DFE, about 200 micrograms DFE to about 8,500 micrograms DFE, about 200 micrograms DFE to about 10,000 micrograms DFE, about 300 micrograms DFE to about 400 micrograms DFE, about 300 micrograms DFE to about 500 micrograms DFE, about 300 micrograms DFE to about 1,000 micrograms DFE, about 300 micrograms DFE to about 5,000 micrograms DFE, about 300 micrograms DFE to about 8,500 micrograms DFE, about 300 micrograms DFE to about 10,000 micrograms DFE, about 400 micrograms DFE to about 500 micrograms DFE, about 400 micrograms DFE to about 1,000 micrograms DFE, about 400 micrograms DFE to about 5,000 micrograms DFE, about 400 micrograms DFE to about 8,500 micrograms DFE, about 400 micrograms DFE to about 10,000 micrograms DFE, about 500 micrograms DFE to about 1,000 micrograms DFE, about 500 micrograms DFE to about 5,000 micrograms DFE, about 500 micrograms DFE to about 8,500 micrograms DFE, about 500 micrograms DFE to about 10,000 micrograms DFE, about 1,000 micrograms DFE to about 5,000 micrograms DFE, about 1,000 micrograms DFE to about 8,500 micrograms DFE, about 1,000 micrograms DFE to about 10,000 micrograms DFE, about 5,000 micrograms DFE to about 8,500 micrograms DFE, about 5,000 micrograms DFE to about 10,000 micrograms DFE, or about 8,500 micrograms DFE to about 10,000 micrograms DFE. In some embodiments, the composition comprises folic acid in the amount of about 5 micrograms DFE, about 8.5 micrograms DFE, about 10 micrograms DFE, about 100 micrograms DFE, about 200 micrograms DFE, about 300 micrograms DFE, about 400 micrograms DFE, about 500 micrograms DFE, about 1,000 micrograms DFE, about 5,000 micrograms DFE, about 8,500 micrograms DFE, or about 10,000 micrograms DFE. In some embodiments, the composition comprises folic acid in the amount of at least about 5 micrograms DFE, about 8.5 micrograms DFE, about 10 micrograms DFE, about 100 micrograms DFE, about 200 micrograms DFE, about 300 micrograms DFE, about 400 micrograms DFE, about 500 micrograms DFE, about 1,000 micrograms DFE, about 5,000 micrograms DFE, or about 8,500 micrograms DFE. In some embodiments, the composition comprises folic acid in the amount of at most about 8.5 micrograms DFE, about 10 micrograms DFE, about 100 micrograms DFE, about 200 micrograms DFE, about 300 micrograms DFE, about 400 micrograms DFE, about 500 micrograms DFE, about 1,000 micrograms DFE, about 5,000 micrograms DFE, about 8,500 micrograms DFE, or about 10,000 micrograms DFE.

Vitamin B12

The compositions disclosed herein may comprise Vitamin B12, or cobalamin. This essential nutrient is vital to many body functions, including, but not limited to, the normal functioning of the brain and nervous system, the formation of blood, and the metabolism of every cell in the body. Particularly, vitamin B12, in certain aspects, is involved in fatty acid and amino acid metabolism, as well as DNA synthesis. Vitamin B12, which in some aspects, is known to be synthesized exclusively by bacteria and archaea, can be naturally found in animal products may be less reliably present in plant products. Thus, in certain aspects, certain dietary preferences and restrictions can increase the risk of and/or contribute to a deficiency in vitamin B12. Moreover, the ability to absorb vitamin B12 can decrease with age, which can contribute to a risk of vitamin B12 deficiency in older adults. Symptoms associated with vitamin B12 deficiency can encompass fatigue, weakness, constipation, and loss of appetite, as well as certain neurological changes such as numbness and tingling in the hands and feet. Crucially, a lack of sufficient vitamin B12 may result in cognitive issues. In some aspects, research has associated vitamin B12 deficiency with memory loss, disorientation, and changes in behavior, which may establish its supplementation as particularly important for maintaining cognitive function in older adults. Ensuring adequate vitamin B12 levels through supplementation can support overall cellular health and neurological function, including cognitive abilities, and contributes to the formation of red blood cells. Furthermore, in additional aspects, vitamin B12 can function to participate in the synthesis of S-adenosylmethionine (SAMe), along with B9 (folate). SAMe is a compound involved in immune function and mood regulation. Incorporating vitamin B12 into a supplement regimen may offer a variety of potential health benefits including, but not limited to, providing support for cellular health, neurological function, cognitive ability, and overall well-being.

In some embodiments, the composition comprises vitamin B12 in the amount of about 2 micrograms to about 1,000 micrograms. In some embodiments, the composition comprises vitamin B12 in the amount of about 2 micrograms to about 5 micrograms, about 2 micrograms to about 10 micrograms, about 2 micrograms to about 50 micrograms, about 2 micrograms to about 100 micrograms, about 2 micrograms to about 150 micrograms, about 2 micrograms to about 200 micrograms, about 2 micrograms to about 250 micrograms, about 2 micrograms to about 500 micrograms, about 2 micrograms to about 750 micrograms, about 2 micrograms to about 1,000 micrograms, about 5 micrograms to about 10 micrograms, about 5 micrograms to about 50 micrograms, about 5 micrograms to about 100 micrograms, about 5 micrograms to about 150 micrograms, about 5 micrograms to about 200 micrograms, about 5 micrograms to about 250 micrograms, about 5 micrograms to about 500 micrograms, about 5 micrograms to about 750 micrograms, about 5 micrograms to about 1,000 micrograms, about 10 micrograms to about 50 micrograms, about 10 micrograms to about 100 micrograms, about 10 micrograms to about 150 micrograms, about 10 micrograms to about 200 micrograms, about 10 micrograms to about 250 micrograms, about 10 micrograms to about 500 micrograms, about 10 micrograms to about 750 micrograms, about 10 micrograms to about 1,000 micrograms, about 50 micrograms to about 100 micrograms, about 50 micrograms to about 150 micrograms, about 50 micrograms to about 200 micrograms, about 50 micrograms to about 250 micrograms, about 50 micrograms to about 500 micrograms, about 50 micrograms to about 750 micrograms, about 50 micrograms to about 1,000 micrograms, about 100 micrograms to about 150 micrograms, about 100 micrograms to about 200 micrograms, about 100 micrograms to about 250 micrograms, about 100 micrograms to about 500 micrograms, about 100 micrograms to about 750 micrograms, about 100 micrograms to about 1,000 micrograms, about 150 micrograms to about 200 micrograms, about 150 micrograms to about 250 micrograms, about 150 micrograms to about 500 micrograms, about 150 micrograms to about 750 micrograms, about 150 micrograms to about 1,000 micrograms, about 200 micrograms to about 250 micrograms, about 200 micrograms to about 500 micrograms, about 200 micrograms to about 750 micrograms, about 200 micrograms to about 1,000 micrograms, about 250 micrograms to about 500 micrograms, about 250 micrograms to about 750 micrograms, about 250 micrograms to about 1,000 micrograms, about 500 micrograms to about 750 micrograms, about 500 micrograms to about 1,000 micrograms, or about 750 micrograms to about 1,000 micrograms. In some embodiments, the composition comprises vitamin B12 in the amount of about 2 micrograms, about 5 micrograms, about 10 micrograms, about 50 micrograms, about 100 micrograms, about 150 micrograms, about 200 micrograms, about 250 micrograms, about 500 micrograms, about 750 micrograms, or about 1,000 micrograms. In some embodiments, the composition comprises vitamin B12 in the amount of at least about 2 micrograms, about 5 micrograms, about 10 micrograms, about 50 micrograms, about 100 micrograms, about 150 micrograms, about 200 micrograms, about 250 micrograms, about 500 micrograms, or about 750 micrograms. In some embodiments, the composition comprises vitamin B12 in the amount of at most about 5 micrograms, about 10 micrograms, about 50 micrograms, about 100 micrograms, about 150 micrograms, about 200 micrograms, about 250 micrograms, about 500 micrograms, about 750 micrograms, or about 1,000 micrograms.

Vitamin B5

The compositions disclosed herein may incorporate Vitamin B5, also known as pantothenic acid, or its derivatives. Pantothenic acid is a water-soluble vitamin that plays a crucial role in the body's energy metabolism. It is a component of coenzyme A (CoA), which is involved in the synthesis and breakdown of proteins, carbohydrates, and fats. Consequently, adequate levels of pantothenic acid can support normal physiological functions including the maintenance of energy levels and overall cellular health. In additional aspects, pantothenic acid can be functionally significant for the synthesis of certain hormones and cholesterol, contributing to the regulation of certain metabolic processes. While pantothenic acid can be available from a wide range of dietary sources, supplementation may be beneficial for certain individuals or situations. With age, digestive efficiency can decrease, potentially leading to a reduced absorption of nutrients, including pantothenic acid.

In such instances, supplementation with pantothenic acid could help maintain optimal levels in the body and support overall well-being. In certain embodiments, compositions provided herein can comprise pantothenic acid in forms including, but not limited to, D-calcium pantothenate, or pantethine.

In some embodiments, the composition comprises vitamin B5 or a derivative thereof in the amount of about 5 milligrams to about 5,000 milligrams. In some embodiments, the composition comprises vitamin B5 or a derivative thereof in the amount of about 5 milligrams to about 10 milligrams, about 5 milligrams to about 100 milligrams, about 5 milligrams to about 150 milligrams, about 5 milligrams to about 200 milligrams, about 5 milligrams to about 250 milligrams, about 5 milligrams to about 500 milligrams, about 5 milligrams to about 1,000 milligrams, about 5 milligrams to about 2,000 milligrams, about 5 milligrams to about 3,000 milligrams, about 5 milligrams to about 4,000 milligrams, about 5 milligrams to about 5,000 milligrams, about 10 milligrams to about 100 milligrams, about 10 milligrams to about 150 milligrams, about 10 milligrams to about 200 milligrams, about 10 milligrams to about 250 milligrams, about 10 milligrams to about 500 milligrams, about 10 milligrams to about 1,000 milligrams, about 10 milligrams to about 2,000 milligrams, about 10 milligrams to about 3,000 milligrams, about 10 milligrams to about 4,000 milligrams, about 10 milligrams to about 5,000 milligrams, about 100 milligrams to about 150 milligrams, about 100 milligrams to about 200 milligrams, about 100 milligrams to about 250 milligrams, about 100 milligrams to about 500 milligrams, about 100 milligrams to about 1,000 milligrams, about 100 milligrams to about 2,000 milligrams, about 100 milligrams to about 3,000 milligrams, about 100 milligrams to about 4,000 milligrams, about 100 milligrams to about 5,000 milligrams, about 150 milligrams to about 200 milligrams, about 150 milligrams to about 250 milligrams, about 150 milligrams to about 500 milligrams, about 150 milligrams to about 1,000 milligrams, about 150 milligrams to about 2,000 milligrams, about 150 milligrams to about 3,000 milligrams, about 150 milligrams to about 4,000 milligrams, about 150 milligrams to about 5,000 milligrams, about 200 milligrams to about 250 milligrams, about 200 milligrams to about 500 milligrams, about 200 milligrams to about 1,000 milligrams, about 200 milligrams to about 2,000 milligrams, about 200 milligrams to about 3,000 milligrams, about 200 milligrams to about 4,000 milligrams, about 200 milligrams to about 5,000 milligrams, about 250 milligrams to about 500 milligrams, about 250 milligrams to about 1,000 milligrams, about 250 milligrams to about 2,000 milligrams, about 250 milligrams to about 3,000 milligrams, about 250 milligrams to about 4,000 milligrams, about 250 milligrams to about 5,000 milligrams, about 500 milligrams to about 1,000 milligrams, about 500 milligrams to about 2,000 milligrams, about 500 milligrams to about 3,000 milligrams, about 500 milligrams to about 4,000 milligrams, about 500 milligrams to about 5,000 milligrams, about 1,000 milligrams to about 2,000 milligrams, about 1,000 milligrams to about 3,000 milligrams, about 1,000 milligrams to about 4,000 milligrams, about 1,000 milligrams to about 5,000 milligrams, about 2,000 milligrams to about 3,000 milligrams, about 2,000 milligrams to about 4,000 milligrams, about 2,000 milligrams to about 5,000 milligrams, about 3,000 milligrams to about 4,000 milligrams, about 3,000 milligrams to about 5,000 milligrams, or about 4,000 milligrams to about 5,000 milligrams. In some embodiments, the composition comprises vitamin B5 or a derivative thereof in the amount of about 5 milligrams, about 10 milligrams, about 100 milligrams, about 150 milligrams, about 200 milligrams, about 250 milligrams, about 500 milligrams, about 1,000 milligrams, about 2,000 milligrams, about 3,000 milligrams, about 4,000 milligrams, or about 5,000 milligrams. In some embodiments, the composition comprises vitamin B5 or a derivative thereof in the amount of at least about 5 milligrams, about 10 milligrams, about 100 milligrams, about 150 milligrams, about 200 milligrams, about 250 milligrams, about 500 milligrams, about 1,000 milligrams, about 2,000 milligrams, about 3,000 milligrams, or about 4,000 milligrams. In some embodiments, the composition comprises vitamin B5 or a derivative thereof in the amount of at most about 10 milligrams, about 100 milligrams, about 150 milligrams, about 200 milligrams, about 250 milligrams, about 500 milligrams, about 1,000 milligrams, about 2,000 milligrams, about 3,000 milligrams, about 4,000 milligrams, or about 5,000 milligrams.

In some embodiments, the composition comprises pantothenic acid in the amount of about 5 milligrams to about 5,000 milligrams. In some embodiments, the composition comprises pantothenic acid in the amount of about 5 milligrams to about 10 milligrams, about 5 milligrams to about 100 milligrams, about 5 milligrams to about 150 milligrams, about 5 milligrams to about 200 milligrams, about 5 milligrams to about 250 milligrams, about 5 milligrams to about 500 milligrams, about 5 milligrams to about 1,000 milligrams, about 5 milligrams to about 2,000 milligrams, about 5 milligrams to about 3,000 milligrams, about 5 milligrams to about 4,000 milligrams, about 5 milligrams to about 5,000 milligrams, about 10 milligrams to about 100 milligrams, about 10 milligrams to about 150 milligrams, about 10 milligrams to about 200 milligrams, about 10 milligrams to about 250 milligrams, about 10 milligrams to about 500 milligrams, about 10 milligrams to about 1,000 milligrams, about 10 milligrams to about 2,000 milligrams, about 10 milligrams to about 3,000 milligrams, about 10 milligrams to about 4,000 milligrams, about 10 milligrams to about 5,000 milligrams, about 100 milligrams to about 150 milligrams, about 100 milligrams to about 200 milligrams, about 100 milligrams to about 250 milligrams, about 100 milligrams to about 500 milligrams, about 100 milligrams to about 1,000 milligrams, about 100 milligrams to about 2,000 milligrams, about 100 milligrams to about 3,000 milligrams, about 100 milligrams to about 4,000 milligrams, about 100 milligrams to about 5,000 milligrams, about 150 milligrams to about 200 milligrams, about 150 milligrams to about 250 milligrams, about 150 milligrams to about 500 milligrams, about 150 milligrams to about 1,000 milligrams, about 150 milligrams to about 2,000 milligrams, about 150 milligrams to about 3,000 milligrams, about 150 milligrams to about 4,000 milligrams, about 150 milligrams to about 5,000 milligrams, about 200 milligrams to about 250 milligrams, about 200 milligrams to about 500 milligrams, about 200 milligrams to about 1,000 milligrams, about 200 milligrams to about 2,000 milligrams, about 200 milligrams to about 3,000 milligrams, about 200 milligrams to about 4,000 milligrams, about 200 milligrams to about 5,000 milligrams, about 250 milligrams to about 500 milligrams, about 250 milligrams to about 1,000 milligrams, about 250 milligrams to about 2,000 milligrams, about 250 milligrams to about 3,000 milligrams, about 250 milligrams to about 4,000 milligrams, about 250 milligrams to about 5,000 milligrams, about 500 milligrams to about 1,000 milligrams, about 500 milligrams to about 2,000 milligrams, about 500 milligrams to about 3,000 milligrams, about 500 milligrams to about 4,000 milligrams, about 500 milligrams to about 5,000 milligrams, about 1,000 milligrams to about 2,000 milligrams, about 1,000 milligrams to about 3,000 milligrams, about 1,000 milligrams to about 4,000 milligrams, about 1,000 milligrams to about 5,000 milligrams, about 2,000 milligrams to about 3,000 milligrams, about 2,000 milligrams to about 4,000 milligrams, about 2,000 milligrams to about 5,000 milligrams, about 3,000 milligrams to about 4,000 milligrams, about 3,000 milligrams to about 5,000 milligrams, or about 4,000 milligrams to about 5,000 milligrams. In some embodiments, the composition comprises pantothenic acid in the amount of about 5 milligrams, about 10 milligrams, about 100 milligrams, about 150 milligrams, about 200 milligrams, about 250 milligrams, about 500 milligrams, about 1,000 milligrams, about 2,000 milligrams, about 3,000 milligrams, about 4,000 milligrams, or about 5,000 milligrams. In some embodiments, the composition comprises pantothenic acid in the amount of at least about 5 milligrams, about 10 milligrams, about 100 milligrams, about 150 milligrams, about 200 milligrams, about 250 milligrams, about 500 milligrams, about 1,000 milligrams, about 2,000 milligrams, about 3,000 milligrams, or about 4,000 milligrams. In some embodiments, the composition comprises pantothenic acid in the amount of at most about 10 milligrams, about 100 milligrams, about 150 milligrams, about 200 milligrams, about 250 milligrams, about 500 milligrams, about 1,000 milligrams, about 2,000 milligrams, about 3,000 milligrams, about 4,000 milligrams, or about 5,000 milligrams.

Para-Aminobenzoic Acid (PABA)

In certain embodiments, the compositions outlined herein may incorporate PABA, or para-aminobenzoic acid. PABA is an organic compound that, though not classified as an essential nutrient, has been associated with various health benefits. PABA serves as an intermediate in the synthesis of folate in bacteria, aiding in metabolic processes. Additionally, PABA has been known to have antioxidant properties, which could help protect the body against damage from free radicals and support overall cellular health. Furthermore, PABA is often incorporated into skincare products due to its potential to improve skin health, including its ability to protect the skin against ultraviolet radiation and improve skin hydration. Aging populations may find supplementation with PABA particularly beneficial, as oxidative stress and skin health issues like dryness or wrinkles are common concerns with aging. Also, it's worth noting that PABA is a component of certain B-complex formulations, although the human requirement for PABA is not clearly defined. The incorporation of PABA into the disclosed supplement aims to provide these potential benefits to the user, promoting cellular health and skin wellness, particularly in populations as they age.

In some embodiments, the composition comprises PABA in the amount of about 10 milligrams to about 5,000 milligrams. In some embodiments, the composition comprises PABA in the amount of about 10 milligrams to about 50 milligrams, about 10 milligrams to about 100 milligrams, about 10 milligrams to about 150 milligrams, about 10 milligrams to about 200 milligrams, about 10 milligrams to about 250 milligrams, about 10 milligrams to about 500 milligrams, about 10 milligrams to about 1,000 milligrams, about 10 milligrams to about 2,000 milligrams, about 10 milligrams to about 3,000 milligrams, about 10 milligrams to about 4,000 milligrams, about 10 milligrams to about 5,000 milligrams, about 50 milligrams to about 100 milligrams, about 50 milligrams to about 150 milligrams, about 50 milligrams to about 200 milligrams, about 50 milligrams to about 250 milligrams, about 50 milligrams to about 500 milligrams, about 50 milligrams to about 1,000 milligrams, about 50 milligrams to about 2,000 milligrams, about 50 milligrams to about 3,000 milligrams, about 50 milligrams to about 4,000 milligrams, about 50 milligrams to about 5,000 milligrams, about 100 milligrams to about 150 milligrams, about 100 milligrams to about 200 milligrams, about 100 milligrams to about 250 milligrams, about 100 milligrams to about 500 milligrams, about 100 milligrams to about 1,000 milligrams, about 100 milligrams to about 2,000 milligrams, about 100 milligrams to about 3,000 milligrams, about 100 milligrams to about 4,000 milligrams, about 100 milligrams to about 5,000 milligrams, about 150 milligrams to about 200 milligrams, about 150 milligrams to about 250 milligrams, about 150 milligrams to about 500 milligrams, about 150 milligrams to about 1,000 milligrams, about 150 milligrams to about 2,000 milligrams, about 150 milligrams to about 3,000 milligrams, about 150 milligrams to about 4,000 milligrams, about 150 milligrams to about 5,000 milligrams, about 200 milligrams to about 250 milligrams, about 200 milligrams to about 500 milligrams, about 200 milligrams to about 1,000 milligrams, about 200 milligrams to about 2,000 milligrams, about 200 milligrams to about 3,000 milligrams, about 200 milligrams to about 4,000 milligrams, about 200 milligrams to about 5,000 milligrams, about 250 milligrams to about 500 milligrams, about 250 milligrams to about 1,000 milligrams, about 250 milligrams to about 2,000 milligrams, about 250 milligrams to about 3,000 milligrams, about 250 milligrams to about 4,000 milligrams, about 250 milligrams to about 5,000 milligrams, about 500 milligrams to about 1,000 milligrams, about 500 milligrams to about 2,000 milligrams, about 500 milligrams to about 3,000 milligrams, about 500 milligrams to about 4,000 milligrams, about 500 milligrams to about 5,000 milligrams, about 1,000 milligrams to about 2,000 milligrams, about 1,000 milligrams to about 3,000 milligrams, about 1,000 milligrams to about 4,000 milligrams, about 1,000 milligrams to about 5,000 milligrams, about 2,000 milligrams to about 3,000 milligrams, about 2,000 milligrams to about 4,000 milligrams, about 2,000 milligrams to about 5,000 milligrams, about 3,000 milligrams to about 4,000 milligrams, about 3,000 milligrams to about 5,000 milligrams, or about 4,000 milligrams to about 5,000 milligrams. In some embodiments, the composition comprises PABA in the amount of about 10 milligrams, about 50 milligrams, about 100 milligrams, about 150 milligrams, about 200 milligrams, about 250 milligrams, about 500 milligrams, about 1,000 milligrams, about 2,000 milligrams, about 3,000 milligrams, about 4,000 milligrams, or about 5,000 milligrams. In some embodiments, the composition comprises PABA in the amount of at least about 10 milligrams, about 50 milligrams, about 100 milligrams, about 150 milligrams, about 200 milligrams, about 250 milligrams, about 500 milligrams, about 1,000 milligrams, about 2,000 milligrams, about 3,000 milligrams, or about 4,000 milligrams. In some embodiments, the composition comprises PABA in the amount of at most about 50 milligrams, about 100 milligrams, about 150 milligrams, about 200 milligrams, about 250 milligrams, about 500 milligrams, about 1,000 milligrams, about 2,000 milligrams, about 3,000 milligrams, about 4,000 milligrams, or about 5,000 milligrams.

Additive Ingredients

The compositions may further include other ingredients such as sweeteners, flavoring agents, preservatives, and other natural supplements, which may confer enhanced palatability, preservation, or added health benefits. Non-limiting examples of such agents may comprise one or more artificial sweeteners, one or more natural sweeteners, one or more flavoring agents, one or more preservatives, or a combination thereof.

Flavoring Agents

Flavoring agents can be an important component for enhancing the palatability of the compositions provided herein and may encourage consistent usage. Flavoring agents may also contribute additional health benefits. For instance, flavonoids (e.g., flavanols), a class of plant and fungus secondary metabolites, may possess antioxidant properties and may contribute to positive health outcomes including supporting cardiovascular health, reducing inflammation, and providing neuroprotective effects. The specific types and amounts of flavoring agents, including flavonoids and flavanols, can be tailored based on the desired taste profile and health goals. For instance, a composition meant for a berry-flavored drink might include a mix of berry-derived flavonoids, while a composition for a cocoa-flavored drink could include flavanols from cocoa. Certain flavoring agents may also influence the rate of saliva production, which can aid in the initial stages of digestion. The selection and combination of flavoring agents can be tailored to create a wide variety of flavor options, catering to different consumer preferences, and making the supplement more enjoyable to consume, thereby encouraging regular and continued use. The addition of such flavoring agents can make the nutritional supplement more enjoyable to consume while also adding value in terms of antioxidant content and potential health benefits.

Sweetening Agents

To enhance the palatability of the disclosed supplement formulation, one or more sweetening agents can be incorporated. These sweetening agents may include, but are not limited to, natural sweeteners such as stevia and monk fruit extract, artificial sweeteners like sucralose, aspartame, or acesulfame potassium, and sugar alcohols such as erythritol, xylitol, or sorbitol. These non-limiting examples of sweeteners can be used individually or in combination to achieve the desired level of sweetness. The type and quantity of sweeteners used can be tailored to accommodate various dietary needs and preferences, helping to ensure the supplement is palatable and enjoyable for all users.

In addition to enhancing the palatability of the disclosed supplement formulation, the selection of one or more of sweetening agents can also confer additional health benefits. For instance, natural sweeteners like stevia not only provide a calorie-free sweetness but have also been associated with health benefits such as lowering blood sugar and blood pressure levels in certain individuals. Similarly, sugar alcohols, such as erythritol, xylitol, or sorbitol, contribute sweetness while providing fewer calories than sugar, which may be beneficial for weight management. They also do not contribute to tooth decay, offering dental health advantages. On the other hand, artificial sweeteners like sucralose, aspartame, or acesulfame potassium, can provide a sweet taste without the added calories, potentially benefiting individuals managing their weight or blood sugar levels.

Preservatives

To ensure the long-term stability and shelf-life of the supplement, it may also be beneficial to incorporate one or more preservatives in the formulation. Preservatives can inhibit the growth of bacteria, yeasts, and molds to help maintain the product's safety, effectiveness, and quality over time. Various types of preservatives can be used, including, but not limited to, natural preservatives such as citric acid, ascorbic acid, or tocopherols, and artificial preservatives like potassium sorbate or sodium benzoate. The inclusion of preservatives in the disclosed supplement formulation can help enhance product stability and prolong shelf life, thereby ensuring consistent nutrient content and quality. While the primary function of preservatives is to improve the long-term stability and shelf-life of the supplement, certain preservatives can also offer secondary health benefits. For instance, natural preservatives such as citric acid and ascorbic acid (vitamin C) not only inhibit the growth of bacteria, yeasts, and molds but also have antioxidant properties that can help protect the body's cells against damage from free radicals. Tocopherols (vitamin E), another type of natural preservative, also have antioxidant properties and can support heart health. Artificial preservatives like potassium sorbate or sodium benzoate are primarily used for their antimicrobial properties, ensuring the product's safety, effectiveness, and quality over time. These additives, used in conjunction with the active ingredients in the disclosed supplement formulation, can help enhance product stability, prolong shelf life, and contribute to the overall health benefits of the supplement.

Methods of Use

Powdered Formulation

Various embodiments of the disclosed compositions may be formulated as a powdered supplement. A powdered formulation may present an alternative mode of nutrient intake, as compared to regimens involving one or more oral capsules with a similar or equivalent nutrient profile. The use of a powdered composition may confer several benefits for a consumer including, but not limited to, convenient mode of administration, increased adherence to a nutritional supplement regimen, and enhanced the bioavailability of the nutrients therein. Consumption of the powdered composition can induce the body to absorb the nutrients comprised therein more readily as compared to solid tablet or capsule alternative supplements. A powdered composition may be particularly advantageous for individuals with various gastrointestinal issues, including, but not limited to, conditions such as irritable bowel syndrome (IBS), inflammatory bowel disease (IBD), gastroesophageal reflux disease (GERD), peptic ulcer disease, and celiac disease, where absorption of nutrients might be compromised. This enhanced bioavailability can also be beneficial for aging populations, as nutrient absorption capacity can decrease with age. Furthermore, the powdered compositions disclosed herein can be formulated to be free of binders and fillers commonly found in tablets, pills, or capsules with similar or equivalent nutrient profiles, which can enhance suitability of the powdered composition for consumers with various conditions and preferences, including, but not limited to food sensitivities and/or allergies. The powdered compositions disclosed herein may additionally confer the benefit of adjustable serving sizes for consumption, which can enable or facilitate customization of nutrient intake based on individual needs, preferences, and/or tolerability, Catering to a range of various consumer needs and preferences, including those of aging populations, the disclosed compositions may provide a practical, user-friendly solution for maintaining optimal nutrient intake.

Packaging and Manufacturing

In certain embodiments, the compositions disclosed herein may be packaged as a powdered formulation with different options available to cater to the diverse needs and preferences of consumers. One possible option is single-serving satchels. This form of packaging provides an easy and convenient option for consumers, especially for those on-the-go. The precisely measured satchels eliminate the need for the consumer to measure out their own dosages, ensuring a consistent nutrient intake with each use. Moreover, the compact and portable nature of the satchels allows consumers to easily bring them along to the gym, office, or while traveling, making it simpler to adhere to their supplement regimen no matter where they are. An alternative mode of packaging and storing may comprise the use of a multi-serving cannister. This form of packaging may provide an economical and environmentally sustainable option for consumers. A multi-serving cannister may particularly be suitable for home or gym use, where a scoop can be used to measure out a pre-determined quantity of the powdered composition. Various packaging options may accommodate a variety of consumer lifestyles and may promote adherence to a nutritional supplement regimen comprising the compositions disclosed herein.

Liquid Formulation

In certain embodiments, the compositions disclosed herein may be formulated as a liquid composition following dissolution of the powdered composition in a suitable solvent. The liquid composition may provide a highly efficient mode of nutrient intake compared to traditional supplement forms such as tablets, pills, or capsules. The liquid nature of the composition may facilitate and/or expedite nutrient absorption, potentially optimizing bioavailability due to the nutrients already being in solution, thus potentially eliminating the need for the body to break down a supplement in solid form. Ingestion of the liquid composition may confer an enhanced degree of bioavailability of one or more of the constituent nutrients, which may lead to a higher nutrient utilization rate. Liquid formulations can provide versatility and can cater to different consumer preferences. For individuals who may have difficulty swallowing pills or tablets, or for those who prefer to avoid consumption of multiple nutrient supplements, a liquid formulation can provide a practical and/or preferred alternative. In certain instances, the liquid composition provides a user-friendly approach to nutrient intake, allowing for customization according to individual needs. The consumer may have an enhanced ability to control and/or vary the concentration of the liquid composition according to their personal health requirements and/or taste preferences. Moreover, the liquid form may eliminate the need for certain excipients that may often be used in the production of tablets, pills, or capsules, making it a cleaner form of nutrient delivery. The combination of these factors—increased bioavailability, improved ease of consumption, customization, and cleaner intake—underline the potential advantages of these liquid formulations. Liquid formulations may also offer advantages that may be particularly beneficial for aging populations. As people age, the ability to swallow pills or tablets can decrease due to various factors such as muscle weakness, reflex changes, or other health issues. Additionally, the absorption of nutrients can decrease with age due to changes in the gastrointestinal tract, but a liquid supplement may promote better absorption, as well as higher adherence to a nutritional supplement regimen.

EXAMPLES

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 1—Compositions for Male Adults

In one embodiment, a composition is formulated for promoting longevity. The ingredients of the composition are as shown in Table 1 (Variation 1) below. The exemplary composition disclosed herein comprises collagen, which contributes about 10 grams to the formulation. For enhanced muscular health and performance, creatine is added at a volume of approximately 5 grams. Various antioxidative components are present in the composition, which include trans-resveratrol at about 500 milligrams, PABA at about 500 milligrams, and vitamin C at about 500 milligrams. Hyaluronic acid and biotin are added for joint, skin, and hair health, with quantities of about 250 milligrams and about 2500 micrograms, respectively. The composition additionally includes elements for cellular and cardiovascular health. These are Coenzyme Q10 (CoQ10), at about 200 milligrams, and spermidine, at about 10 milligrams. B-vitamins in the form of pantothenic acid (vitamin B5), folate (vitamin B9), and vitamin B12, are also included, each at about 500 milligrams, 1000 micrograms and about 100 micrograms, respectively. Finally, the composition comprises nicotinamide riboside (NR) at about 500 milligrams. In certain examples, this composition is formulated for a male adult. In some instances, the male adult is at least 50 years of age.

TABLE 1

| Compositions for Promoting Longevity | | |
| --- | --- | --- |
| Ingredients | Weight (Variation 1) | Weight (Variation 2) |
| Whey Protein Isolate | — | 10 g |
| Collagen | 10 g | 10 g |
| Creatine | 5 g | 5 g |
| Trans-resveratrol | 500 mg | 500 mg |
| Vitamin C | 500 mg | 500 mg |
| Hyaluronic Acid | 250 mg | 250 mg |
| Biotin | 2500 mcg | 2500 mcg |
| CoQ10 | 200 mg | 200 mg |
| Spermidine | 10 mg | 10 mg |
| Folate | 1000 mcg | 400 mcg |
| Vitamin B12 | 100 mcg | 2.4 mcg |
| Pantothenic Acid (Vitamin B5) | 500 mg | 500 mg |
| PABA | 500 mg | 500 mg |
| NR | 500 mg | 500 mg |

Example 2—Compositions for Promoting Muscle Growth, Recovery, and Endurance

In one embodiment, the composition is formulated for promoting muscle growth, recovery, and endurance. The ingredients are as listed in Table 1 (Variation 2) above. The composition further comprises whey protein isolate at about 10 grams. The antioxidative components, joint, skin, and hair health components, and elements for cellular and cardiovascular health are maintained at the same quantities as in Example 1. However, the vitamin components have been adjusted, with folate (Vitamin B9) and Vitamin B12 each at about 1200 micrograms and about 120 micrograms, respectively, which may be suitable for adult women. The NAD$^+$ precursor, nicotinamide riboside (NR), is included at about 500 milligrams. In certain examples, this composition is formulated for a female adult. In some instances, the composition is administered as a powdered composition.

Example 2—Compositions for Female Adults

In one embodiment, a composition for promoting longevity is formulated for female adults. The ingredients are as listed in Table 2 (Variation 1) below. Like in Example 1, the primary protein sources are whey protein isolate and collagen, each contributing about 10 grams. Creatine is added at a slightly lower volume of about 4 grams to adjust for typical differences in muscle mass between males and females. The antioxidative components, joint, skin, and hair health components, and elements for cellular and cardiovascular health are maintained at the same quantities as in Example 1. However, the vitamin components have been adjusted, with folate (Vitamin B9) and Vitamin B12 each at about 1200 micrograms and about 120 micrograms, respectively, to address the specific nutritional needs of women in certain instances. The NAD$^+$ precursor, nicotinamide riboside (NR), is included at about 500 milligrams. In some instances, the composition is administered as a powdered composition.

TABLE 2

Example Compositions

| Ingredients | Quantity (Variation 1) | Quantity (Variation 2) | Quantity (Variation 3) |
| --- | --- | --- | --- |
| Plant-based Protein | — | — | 10 g |
| Whey Protein Isolate | — | 15 g | — |
| Collagen | 10 g | 10 g | 10 g |
| Creatine | 4 g | 3 g | 5 g |
| Trans-resveratrol | 500 mg | 500 mg | 150 mg |
| Vitamin C | 500 mg | 500 mg | 75 mg |
| Hyaluronic Acid | 250 mg | 250 mg | 200 mg |
| Biotin | 2500 mcg | 2500 mcg | 30 mcg |
| CoQ10 | 200 mg | 200 mg | 200 mg |
| Spermidine | 10 mg | 10 mg | 10 mg |
| Folate | 1200 mcg | 400 mcg | 400 mcg |
| Vitamin B12 | 120 mcg | 2.4 mcg | 2.4 mcg |
| Pantothenic Acid (Vitamin B5) | 500 mg | 500 mg | 5 mcg |
| PABA | 500 mg | 500 mg | 500 mg |
| NMN | 500 mg | 500 mg | — |
| NR | — | — | 500 mg |

Example 3—Effect on Longevity

An individual consumes the composition detailed in Table 2 (Variation 1) daily for a period of one year to increase muscle mass, improve skin, hair, and joint health and enhanced cellular and enhance cardiovascular health, which may result in improved longevity and delayed onset of aging in the individual. In some instances, the composition is administered as a powdered composition.

Example 4—Effect on Muscle Growth and Recovery

In one embodiment, an individual partaking in regular resistance training orally consumes the composition detailed in Table 1 (Variation 2) daily for a period of six months for enhanced muscle growth, improved muscle recovery post-workout, and overall enhanced athletic performance. In some instances, the individual is an adult male. In some instances, the individual is an adult female. In some instances, the composition is administered as a powdered composition.

Example 5—Composition for Maintenance of Daily Nutrition

An individual orally consumes the composition detailed in Table 2 (Variation 3) to maintain daily recommended levels of various nutrients. In some instances, the individual is an adult male. In some instances, the individual is an adult female. In some instances, the composition is administered as a powdered composition.

Example 6—Preparation of a Powdered Formulation

In one embodiment, each component as shown below in Table 3 is procured, then ground or milled into a fine powder. In a dry environment, the components are weighed to incorporate the appropriate quantities of each component into a mixture. The components are mixed thoroughly, for instance, in multiple stages, to form a homogenous mixture. In some instances, the mixture is packaged into single-serving satchels comprising from about 35 grams to about 40 grams of the mixture per serving per satchel. In some instances, the mixture is packaged into a multi-serving cannister comprising from about 15 servings to about 60 servings, wherein each serving comprises about 35 grams to about 40 grams of the packaged mixture.

TABLE 3

Powdered Compositions for Manufacturing and Packaging

| Ingredients | Quantity (mg) |
| --- | --- |
| Source of Dietary Protein | 5,000-25,000 |
| Collagen | 5,000-25,000 |
| Creatine | 1,000-15,000 |
| Trans-resveratrol | 100-2,000 |
| Vitamin C or a derivative thereof | 100-2,000 |
| Hyaluronic Acid | 50-1,000 |
| Biotin | 0.005-25 |
| CoQ10 | 50-1,000 |
| Spermidine | 1-1,000 |
| Folate or a derivative thereof (e.g., folic acid) | 0.005-5 |
| Vitamin B12 or a derivative thereof | 0.005-1 |
| Pantothenic Acid (Vitamin B5) | 0.005-1 |
| PABA | 10-5,000 |
| Pre-cursor of NAD$^+$ (e.g., NMN, NR, etc.) | 50-2,000 |

Example 7—Preparation of a Liquid Composition

In one embodiment, a powdered composition is formulated in accordance with the ingredients and quantities set forth in Table 3. A single serving of the powdered formulation (e.g., about 39 grams) is added to a quantity of a suitable liquid solvent (e.g., water, plant-based milk, animal-based milk) in an amount sufficient to fully dissolve the powdered formulation (e.g., from about 8 fluid ounces to about 16 fluid ounces). The mixture is agitated (e.g., stirred, inverted, shaken, etc.) until the powdered composition is fully dissolved into the solvent. Upon dissolution of the powdered composition, the mixture is consumed immediately or stored for later consumption. In some instances, refrigeration of the composition is required after mixing. In some instances, the mixture is packaged into a vessel (e.g., sealable bottle) and stored in a sealed container for future consumption. In some instances, the vessel contains one or more servings of the mixture.

What is claimed is:

1. A composition comprising
(a) about 10 grams of collagen;
(b) about 5 grams of creatine;
(c) about 500 milligrams of trans-resveratrol;
(d) about 10 milligrams of spermidine and
ii. five or more of:
(a) about 500 milligrams of vitamin C;
(b) about 200 milligrams of CoQ10;
(c) about 1,000 micrograms of folate;
(d) about 100 micrograms of vitamin B12;
(e) about 500 milligrams of vitamin B5;
(f) about 500 milligrams of para-aminobenzoic acid (PABA);
(g) about 250 milligrams of one or more precursors of NAD$^+$;
(h) about 50 milligrams to about 300 milligrams of hyaluronic acid
(i) about 2,500 micrograms of biotin, and wherein the composition further comprises a source of dietary protein, wherein the source of dietary protein is an animal-based protein source, a plant-based protein source, or a combination thereof.

2. The composition of claim 1, wherein the precursor of NAD+ is/are selected from the group consisting of nicotinamide, NR, NMN, and niacin.

3. The composition of claim 1, wherein the vitamin B5 is present in the composition in the form of pantothenic acid, D-calcium pantothenate, pantethine, or a combination thereof.

4. The composition of 1, wherein the composition further comprises a liquid solvent.

5. The composition of claim 4, wherein the liquid solvent comprises one or more of:
(a) water
(b) an animal-based milk; and
(c) a plant-based milk.

6. The composition of claim 5, wherein the plant-based milk is selected from the group consisting of soy milk, almond milk, oat milk, pea milk, rice milk, coconut milk, and macadamia nut milk.

7. The composition of claim 1, wherein the composition further comprises one or more sweetening agents selected from the group consisting of sucralose, *stevia*, aspartame, acesulfame potassium, xylitol, and erythritol.

8. The composition of claim 1, wherein the composition further comprises one or more flavoring agents selected from the group consisting of natural flavors, artificial flavors, cocoa powder, vanillin, citric acid, maltodextrin, a flavonoid, and a flavanol.

9. The composition of claim 1, wherein the composition comprises at least 30 grams of the source of dietary protein.

10. The composition of claim 1, wherein the composition comprises about 34 grams of the source of dietary protein.

11. The composition of claim 1, wherein the source of dietary protein is whey protein isolate.

12. The composition of claim 1, wherein the composition is formulated as a powdered composition.

13. The composition of claim 4, wherein the composition is formulated as a powdered composition.

14. A method of promoting longevity to a human subject in need thereof, the method comprising: administering the composition of claim 13 to the human subject, wherein the composition is combined with about 8 fluid ounces to about 16 fluid ounces of a liquid solvent to form a liquid composition, wherein the administering is achieved via oral ingestion of the liquid composition.

15. The method of claim 14, wherein about 35 grams to about 40 grams of the composition is combined with the liquid solvent.

16. The method of claim 15, wherein the administering is once daily.

* * * * *